(12) United States Patent
Keasler et al.

(10) Patent No.: US 9,374,999 B2
(45) Date of Patent: Jun. 28, 2016

(54) BIOCIDE COMPOSITIONS

(71) Applicant: Ecolab USA Inc., Eagan, MN (US)

(72) Inventors: Victor Keasler, Sugar Land, TX (US); Jeffery Caleb Clark, Campinas (BR); Carrie Keller-Schultz, Houston, TX (US); Brian Bennett, Sugar Land, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 14/448,196

(22) Filed: Jul. 31, 2014

(65) Prior Publication Data

US 2015/0038470 A1 Feb. 5, 2015

Related U.S. Application Data

(60) Provisional application No. 61/861,803, filed on Aug. 2, 2013.

(51) Int. Cl.
| | | |
|---|---|---|
| *A01N 33/12* | (2006.01) | |
| *A01N 43/50* | (2006.01) | |
| *A01N 57/34* | (2006.01) | |

(52) U.S. Cl.
CPC ............... *A01N 33/12* (2013.01); *A01N 43/50* (2013.01)

(58) Field of Classification Search
None
See application file for complete search history.

(56) References Cited

U.S. PATENT DOCUMENTS

| | | | |
|---|---|---|---|
| 6,338,819 B1 | 1/2002 | Braga et al. | |
| 6,488,868 B1 | 12/2002 | Meyer | |
| 6,517,617 B1 * | 2/2003 | Chartier | C11D 1/86 106/14.16 |
| 7,057,050 B2 | 6/2006 | Meyer | |
| 7,951,754 B2 | 5/2011 | Tiwari et al. | |

FOREIGN PATENT DOCUMENTS

WO 2012-135016 10/2012

* cited by examiner

*Primary Examiner* — Samantha Shterengarts
(74) *Attorney, Agent, or Firm* — Senniger Powers LLP

(57) ABSTRACT

Disclosed are biocide compositions. The compositions are useful in applications relating to the production, transportation, storage, and separation of crude oil and natural gas. Also disclosed are methods of using the compositions, particularly in applications relating to the production, transportation, storage, and separation of crude oil and natural gas.

22 Claims, 7 Drawing Sheets

BIOCIDE COMPOSITIONS

CROSS-REFERENCE TO RELATED APPLICATIONS

This application claims the benefit of U.S. Provisional Patent Application Ser. No. 61/861,803, filed Aug. 2, 2013, the entirety of which is herein incorporated by reference.

FIELD OF THE INVENTION

The present disclosure relates generally to biocides, and more particularly to biocides including an imidazoline (e.g., acrylated imidazoline), a quaternary amine, and a phosphonium compound (e.g., tetrakis-(hydroxymethyl) phosphonium sulfate).

BACKGROUND OF THE INVENTION

Oilfield systems are subjected to increased risks associated with microbial control including: $H_2S$ production, microbial influenced corrosion (MIC) and biofouling. When MIC is suspected in a system, the main area of concern becomes the biofilm, or sessile organisms, on the surface of the pipeline. It is widely recognized, within the industry, that in order to be effective at controlling the bacteria within a system there should be a focus on minimizing biofilm regrowth kinetics following treatment (sessile control) in addition to providing sufficient planktonic kill. While tetrakis-(hydroxymethyl) phosphonium sulfate, glutaraldehyde, and quaternary ammonium compounds are widely used as biocides, their efficacy is limited when considering their ability to delay the regrowth kinetics of biofilms after biocide treatment. Thus, there is an increased need, in the oilfield industry, to provide microbial kill and biofilm control, and in particular, to penetrate and delay the regrowth kinetics of biofilms.

SUMMARY OF THE INVENTION

In one aspect, disclosed is a biocide composition including: an imidazoline compound; a quaternary amine; and a phosphonium compound.

The imidazoline compound has formula (I),

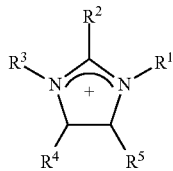

(I)

wherein $R^1$, $R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, $-COR^6$, $-CO_2R^7$, $-SO_3R^8$, $-PO_3H_2$, $-CON(R^9)(R^{10})$, $-OR^{11}$, and $-N(R^{12})(R^{13})$;

$R^2$ is a radical derived from a fatty acid;

$R^3$ is selected from a radical derived from an unsaturated acid;

$R^6$, $R^7$, $R^8$, $R^9$, $R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, $-COR^{14}$, $-CO_2R^{15}$, -alkyl-$COR^{16}$, and -alkyl-$CO_2R^{17}$; and $R^{14}$, $R^{15}$, $R^{16}$, and $R^{17}$ are each independently, at each occurrence, selected from hydrogen, alkyl, and alkenyl.

For compounds of formula (I), $R^1$ can be unsubstituted $C_2$-$C_6$-alkyl; $R^2$ is $-C_{17}H_{35}$, $-C_{17}H_{33}$, or $-C_{17}H_{31}$; $R^3$ is $-CH_2CH_2CO_2R^e$, wherein $R^e$ is hydrogen, $C_1$-$C_6$-alkyl, or $R^e$ is absent; $R^4$ is hydrogen; and $R^5$ is hydrogen.

For compounds of formula (I), $R^1$ can be linear $C_2$-alkyl, substituted with one substituent that is a terminal $-N(R^{12})(R^{13})$, wherein $R^{12}$ is hydrogen and $R^{13}$ is $-COR^{14}$, wherein $R^{14}$ is $-C_{17}H_{35}$, $-C_{17}H_{33}$, or $-C_{17}H_{31}$; $R^2$ is $-C_{17}H_{35}$, $-C_{17}H_{33}$, or $-C_{17}H_{31}$; $R^3$ is $-CH_2CH_2CO_2R^e$, wherein $R^e$ is hydrogen, $C_1$-$C_6$-alkyl, or $R^e$ is absent; $R^4$ is hydrogen; and $R^5$ is hydrogen.

For compounds of formula (I), $R^1$ can be linear $C_2$-alkyl, substituted with one substituent that is a terminal $-N(R^{12})(R^{13})$, wherein $R^{12}$ and $R^{13}$ are each a $-C_2$-alkyl-$CO_2R^{17}$, wherein $R^{17}$ is hydrogen or is absent; $R^2$ is $-C_{17}H_{35}$, $-C_{17}H_{33}$, or $-C_{17}H_{31}$; $R^3$ is $-CH_2CH_2CO_2R^e$, wherein $R^e$ is hydrogen, $C_1$-$C_6$-alkyl, or $R^e$ is absent; $R^4$ is hydrogen; and $R^5$ is hydrogen.

Further, the imidazoline compound can has formula (II),

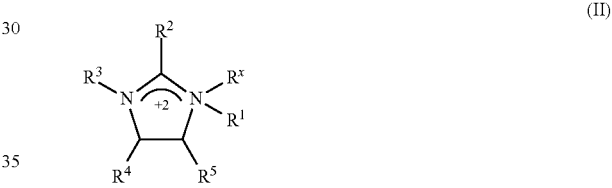

(II)

wherein $R^1$, $R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, $-COR^6$, $-CO_2R^7$, $-SO_3R^8$, $-PO_3H_2$, $-CON(R^9)(R^{10})$, $-OR^{11}$, and $-N(R^{12})(R^{13})$;

$R^2$ is a radical derived from a fatty acid;

$R^3$ and $R^x$ are each independently selected from a radical derived from an unsaturated acid;

$R^6$, $R^7$, $R^8$, $R^9$, $R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, $-COR^{14}$, $-CO_2R^{15}$, -alkyl-$COR^{16}$, and -alkyl-$CO_2R^{17}$; and $R^{14}$, $R^{15}$, $R^{16}$, and $R^{17}$ are each independently, at each occurrence, selected from hydrogen, alkyl, and alkenyl.

For a compound of formula (2), $R^1$ can be unsubstituted $C_2$-$C_6$-alkyl; $R^2$ is $-C_{17}H_{35}$, $-C_{17}H_{33}$, or $-C_{17}H_{31}$; $R^3$ is $-CH_2CH_2CO_2R^e$, wherein $R^e$ is hydrogen, $C_1$-$C_6$-alkyl, or $R^e$ is absent; $R^x$ is $-CH_2CH_2CO_2R^e$, wherein $R^e$ is hydrogen, $C_1$-$C_6$-alkyl, or $R^e$ is absent; $R^4$ is hydrogen; and $R^5$ is hydrogen.

For a compound of formula (2), $R^1$ can be linear $C_2$-alkyl, substituted with one substituent that is a terminal $-N(R^{12})(R^{13})$, wherein $R^{12}$ is hydrogen and $R^{13}$ is $-COR^{14}$, wherein $R^{14}$ is $-C_{17}H_{35}$, $-C_{17}H_{33}$, or $-C_{17}H_{31}$; $R^2$ is $-C_{17}H_{35}$, —$C_{17}H_{33}$, or —$C_{17}H_{31}$; $R^3$ is —$CH_2CH_2CO_2R^e$, wherein $R^e$ is hydrogen, $C_1$-$C_6$-alkyl, or $R^e$ is absent; $R^x$ is —$CH_2CH_2CO_2R^e$, wherein $R^e$ is hydrogen, $C_1$-$C_6$-alkyl, or $R^e$ is absent; $R^4$ is hydrogen; and $R^5$ is hydrogen.

For a compound of formula (2), $R^1$ can be linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or is absent; $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen, $C_1$-$C_6$-alkyl, or $R^e$ is absent; $R^x$ is —$CH_2CH_2CO_2R^e$, wherein $R^e$ is hydrogen, $C_1$-$C_6$-alkyl, or $R^e$ is absent; $R^4$ is hydrogen; and $R^5$ is hydrogen.

Additionally, the imidazoline compound can have a structure of formula (III),

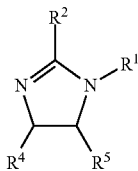

(III)

wherein $R^1$, $R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, —$COR^6$, —$CO_2R^7$, —$SO_3R^8$, —$PO_3H_2$, —$CON(R^9)(R^{10})$, —$OR^{11}$, and —$N(R^{12})(R^{13})$;

$R^2$ is a radical derived from a fatty acid;

$R^6$, $R^7$, $R^8$, $R^9$, $R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, —$COR^{14}$, —$CO_2R^{15}$, -alkyl-$COR^{16}$, and -alkyl-$CO_2R^{17}$; and $R^{14}$, $R^{15}$, $R^{16}$, and $R^{17}$ are each independently, at each occurrence, selected from hydrogen, alkyl, and alkenyl.

For compounds of formula (3), $R^1$ can be unsubstituted $C_2$-$C_6$-alkyl; $R^2$ is —$C_{17}H_{35}$, —$C_{17}H_{33}$, or —$C_{17}H_{31}$; $R^4$ is hydrogen; and $R^5$ is hydrogen.

For a compound of formula (3), $R^1$ can be linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_{17}H_{33}$, or —$C_{17}H_{31}$; $R^2$ is —$C_{17}H_{35}$, —$C_{17}H_{33}$, or —$C_{17}H_{31}$; $R^4$ is hydrogen; and $R^5$ is hydrogen.

For a compound of formula (3), $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or is absent; $R^2$ is —$C_{17}H_{35}$, —$C_{17}H_{33}$, or —$C_{17}H_{31}$; $R^4$ is hydrogen; and $R^5$ is hydrogen.

The quaternary amine can have the formula

[$N^+R^{5a}R^{6a}R^{7a}R^{8a}$][$X^-$]

wherein $R^{5a}$, $R^{6a}$, $R^{7a}$, and $R^{8a}$ are each independently selected from substituted or unsubstituted $C_1$-$C_{18}$-alkyl; and X is Cl, Br or I.

For the quaternary amine, $R^{5a}$, $R^{6a}$, $R^{7a}$, and $R^{8a}$ can each independently be selected from the group consisting of unsubstituted $C_1$-$C_{18}$-alkyl, $C_1$-$C_{18}$-hydroxyalkyl, and benzyl.

The quaternary amine can be selected from the group consisting of tetramethyl ammonium chloride, tetraethyl ammonium chloride, tetrapropyl ammonium chloride, tetrabutyl ammonium chloride, tetrahexyl ammonium chloride, tetraoctyl ammonium chloride, benzyltrimethyl ammonium chloride, benzyltriethyl ammonium chloride, phenyltrimethyl ammonium chloride, phenyltriethyl ammonium chloride, cetyl benzyldimethyl ammonium chloride, hexadecyl trimethyl ammonium chloride, dimethyl $C_{12-16}$-alkyl benzyl ammonium chloride, monomethyl di-$C_{12-16}$-alkyl benzyl quaternary ammonium chloride, benzyl triethanolamine quaternary ammonium chloride, benzyl dimethylaminoethanolamine quaternary ammonium chloride, cocoalkyl dimethyl benzyl ammonium chloride, and combinations thereof.

The phosphonium compound can be selected from the group consisting of alkyltris(hydroxyorgano)phosphonium salts, alkenyltris(hydroxyorgano)phosphonium salts, tetrakis(hydroxyorgano)phosphonium salts, and combinations thereof.

Further, the phosphonium compound can be selected from the group consisting of $C_1$-$C_3$-alkyltris(hydroxymethyl)phosphonium salts, $C_2$-$C_3$-alkenyltris(hydroxymethyl)phosphonium salts, tetrakis(hydroxymethyl)phosphonium salts, and combinations thereof.

Additionally, the phosphonium compound can be selected from the group consisting of tetrakis(hydroxymethyl)phosphonium sulphate (THPS), tetrakis(hydroxymethyl)phosphonium chloride, tetrakis(hydroxymethyl)phosphonium phosphate, tetrakis(hydroxymethyl)phosphonium formate, tetrakis(hydroxymethyl)phosphonium acetate, tetrakis(hydroxymethyl)phosphonium oxalate, and combinations thereof.

The composition can further include a demulsifier. The demulsifier can be selected from the group consisting of dodecylbenzylsulfonic acid (DDBSA), the sodium salt of xylenesulfonic acid (NAXSA), epoxylated and propoxylated compounds, anionic cationic and nonionic surfactants, and resins, phenolic and epoxide resins, and combinations thereof.

The composition can further comprise one or more additional components, each component independently selected from the group consisting of corrosion inhibitors, solvents, asphaltene inhibitors, paraffin inhibitors, scale inhibitors, emulsifiers, water clarifiers, dispersants, gas hydrate inhibitors, biocides, pH modifiers, and surfactants.

In another aspect, disclosed is a method of controlling biofouling, the method comprising providing an effective amount of a composition of the invention into a system. The method can include controlling microbe proliferation in a system used in the production, transportation, storage, and separation of crude oil and natural gas. The method can include controlling microbe proliferation in a system used in a coal-fired process, a waste-water process, a farm, a slaughter house, a land-fill, a municipality waste-water plant, a coking coal process, or a biofuel process.

The compounds, compositions, methods and processes are further described herein.

DETAILED DESCRIPTION

Figure 1:
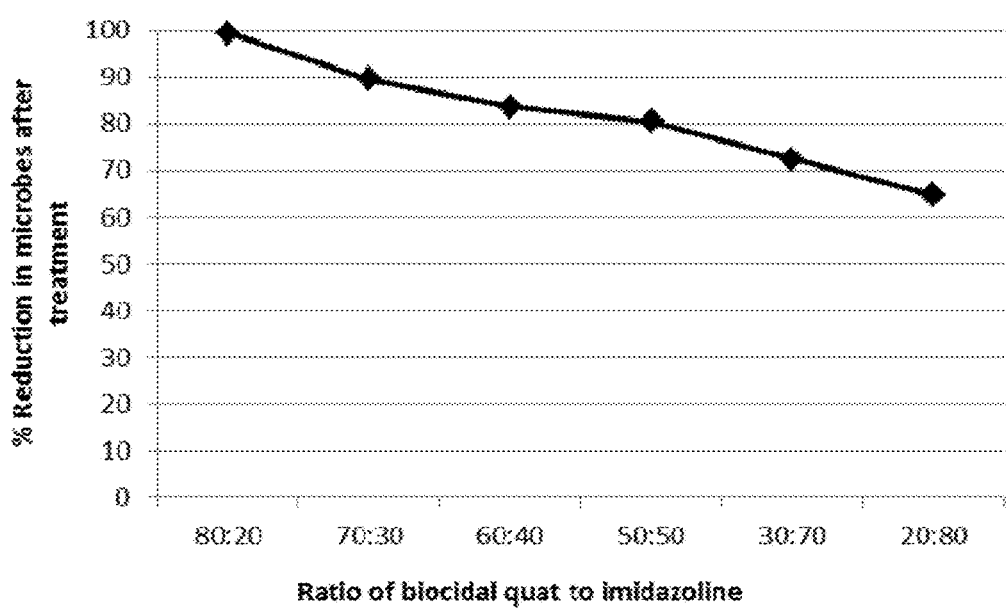
FIG. 1 depicts biocidal activity of compositions including a quaternary amine and an imidazoline.

Disclosed herein are biocide compositions, methods of using said compositions, and processes for their preparation. The compositions include a synergistic combination of at least one imidazoline compound, at least one quaternary amine, and at least one phosphonium compound. The compositions can further include an emulsion breaker to facilitate oil/water separation in the system being treated.

The compositions are particularly useful for controlling microbe proliferation in equipment used in the production, transportation, storage, and separation of crude oil and natural gas. The compositions kill planktonic and sessile microorganisms and provide enhanced control of biofilm kinetic regrowth (sessile control). The compositions are effective against common oilfield microbes (e.g., sulfate reducing and acid producing bacteria), including genera such as *Desulfovibrio, Desulfomicrobium, Shewanella, Clostridium*, and *Pseudomonas*, amongst others. The compositions thus reduce the required biocide treatment rate and treatment frequency compared to biocides currently on the market.

1. Definition of Terms

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups can be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups can be unsubstituted or substituted by one or more suitable substituents, as defined above.

The term "alkynyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon triple bonds. Alkynyl groups include, but are not limited to, ethynyl, propynyl, and butynyl. Alkynyl groups can be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "arylalkyl," as used herein, refers to an aryl group attached to the parent molecular moiety through an alkyl group. Arylalkyl groups can be unsubstituted or substituted by one or more suitable substituents, as defined above.

The term "alkylarylalkyl," as used herein, refers to an alkylaryl group attached to the parent molecular moiety through an alkyl group. Alkylarylalkyl groups can be unsubstituted or substituted by one or more suitable substituents, as defined above.

The term "carbonyl," "(C=O)," or "—C(O)—" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups can be unsubstituted or substituted by one or more suitable substituents, preferably 1 to 5 suitable substituents, as defined above.

The term "cycloalkylalkyl," as used herein, refers to a cycloalkyl group attached to the parent molecular moiety through an alkyl group. Cycloalkylalkyl groups can be unsubstituted or substituted by one or more suitable substituents, as defined above.

The term "alkylcycloalkylalkyl," as used herein, refers to a cycloalkylalkyl group substituted by one or more alkyl groups. Alkylcycloalkylalkyl groups can be unsubstituted or substituted by one or more suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups can be unsubstituted or substituted by one or more suitable substituents, preferably 1 to 5 suitable substituents, as defined above.

The term "heteroarylalkyl," as used herein, refers to a heteroaryl group attached to the parent molecular moiety through an alkyl group. Heteroarylalkyl groups can be unsubstituted or substituted by one or more suitable substituents, as defined above.

The term "alkylheteroarylalkyl," as used herein, refers to a heteroarylalkyl group substituted by one or more alkyl groups. Alkylheteroarylalkyl groups can be unsubstituted or substituted by one or more suitable substituents, as defined above.

The term "heterocycle" or "heterocyclyl," as used herein, refers to a monocyclic, bicyclic, or tricyclic group containing 1 to 4 heteroatoms selected from N, O, S(O)$_n$, P(O)$_n$, PR$^z$, NH or NR$^z$, wherein R$^z$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups can be unsubstituted or substituted by one or more suitable substituents, preferably 1 to 3 suitable substituents, as defined above.

The term "heterocyclylalkyl," as used herein, refers to a heterocycle group attached to the parent molecular moiety through an alkyl group. Heterocyclylalkyl groups can be unsubstituted or substituted by one or more suitable substituents, as defined above.

The term "alkylheterocyclylalkyl," as used herein refers to a heterocyclylalkyl group substituted by one or more alkyl groups. Alkylheterocyclylalkyl groups can be unsubstituted or substituted by one or more suitable substituents, as defined above.

The term "hydroxy," as used herein, refers to an —OH group.

The term "oxo," as used herein, refers to a double bonded oxygen (=O) radical wherein the bond partner is a carbon atom. Such a radical can also be thought as a carbonyl group.

The term "acrylate," as used herein, refers to the material resulting from the Michael addition of acrylic acid to an imidazoline. The addition of this chemical moiety to the imidazoline increases its water solubility, enabling it to reach metal surfaces which are submerged beneath an aqueous layer.

The term "TOFA," as used herein, refers to a tall oil fatty acid that is a distilled product derived from trees and includes a mixture of fatty acids, $C_{17}H_{31-35}COOH$ with a CAS No. 61790-12-3. It is a mixture of oleic acid as a major component, linoleic acid and saturated fatty acids (e.g., about 46% oleic acid, about 41% linoleic acid, about 4% stearic acid, and about 9% other acids).

The term "decyl", as used herein, means a —$C_{10}H_{21}$ alkyl radical, also referred to as "capryl".

The term "dodecyl", as used herein, means a —$C_{12}H_{25}$ alkyl radical, also referred to as "lauryl".

The term "hexadecyl", as used herein, means a —$C_{16}H_{33}$ alkyl radical, also referred to as "palmityl".

The term "hexyl", as used herein, means a —$C_6H_{13}$ alkyl radical, also referred to as "caproyl".

The term "octadecadienyl", as used herein, means a cis, cis-9,12-octadecadienyl radical, also referred to as "linoleyl".

The term "octadecenyl", as used herein, means a cis-9-octadecenyl radical, also referred to as "oleyl".

The term "octadecyl", as used herein, means a —$C_{18}H_{37}$ alkyl radical, also referred to as "stearyl".

The term "octyl", as used herein, means a —$C_8H_{17}$ alkyl radical, also referred to as "caprylyl."

The term "tetradecyl", as used herein, means a —$C_{14}H_{29}$ alkyl radical, also referred to as "myristyl".

The term "myristoleic acid" or "(Z)-tetradec-9-enoic acid," as used herein, refers to

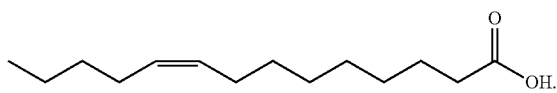 [SMILES: CCCC/C=C\CCCCCCCC(=O)O]

The term "palmitoleic acid" or "(Z)-hexadec-9-enoic acid," as used herein, refers to

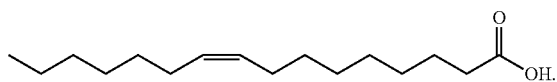 [SMILES: CCCCCC/C=C\CCCCCCCC(=O)O]

The term "sapienic acid" or "(Z)-hexadec-6-enoic acid," as used herein, refers to

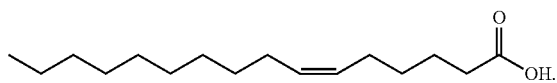 [SMILES: CCCCCCCCC/C=C\CCCCC(=O)O]

The term "oleic acid" or "(Z)-octadec-9-enoic acid," as used herein, refers to

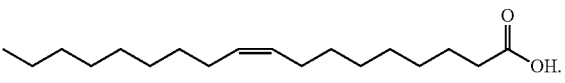 [SMILES: CCCCCCCC/C=C\CCCCCCCC(=O)O]

The term "elaidic acid" or "(E)-octadec-9-enoic acid," as used herein, refers to

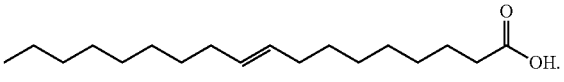 [SMILES: CCCCCCCC/C=C/CCCCCCCC(=O)O]

The term "vaccenic acid" or "(E)-octadec-11-enoic acid," as used herein, refers to

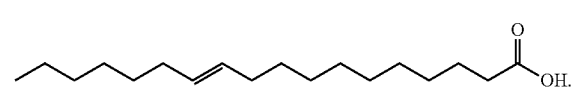 [SMILES: CCCCCC/C=C/CCCCCCCCCC(=O)O]

The term "linoleic acid" or "(9Z,12Z)-octadeca-9,12-dienoic acid," as used herein, refers to

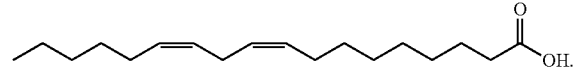

The term "linoelaidic acid" or "(9E,12E)-octadeca-9,12-dienoic acid," as used herein, refers to

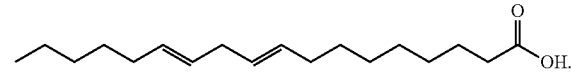 [SMILES: CCCCC/C=C/C/C=C/CCCCCCCC(=O)O]

The term "α-linolenic acid" or "(9Z,12Z,15Z)-octadeca-9,12,15-trienoic acid," as used herein, refers to

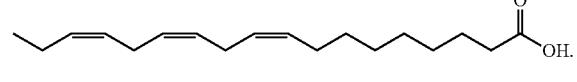

The term "arachidonic acid" or "(5Z,8Z,11Z,14Z)-icosa-5,8,11,14-tetraenoic acid," as used herein, refers to

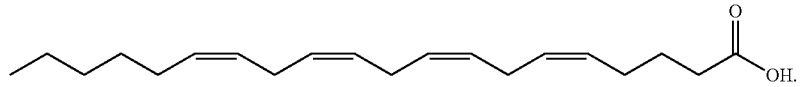

The term "eicosapentaenoic acid" or "(5Z,8Z,11Z,14Z,17Z)-icosa-5,8,11,14,17-pentaenoic acid," as used herein, refers to

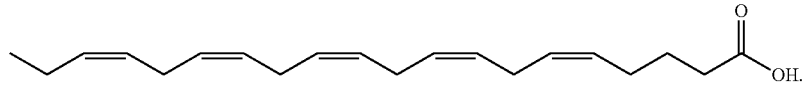 [SMILES: CC/C=C\C/C=C\C/C=C\C/C=C\C/C=C\CCCC(=O)O]

The term "erucic acid" or "(Z)-docos-13-enoic acid," as used herein, refers to

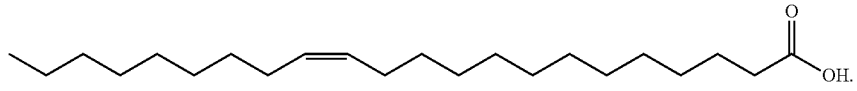 [SMILES: CCCCCCCC/C=C\CCCCCCCCCCCC(=O)O]

The term "docosahexaenoic acid" or "(4Z,7Z,10Z,13Z,16Z,19Z)-docosa-4,7,10,13,16,19-hexaenoic acid," as used herein, refers to

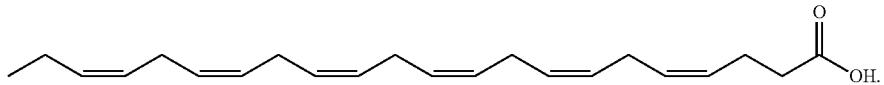 [SMILES: CC/C=C\C/C=C\C/C=C\C/C=C\C/C=C\C/C=C\CCC(=O)O]

The term "hexadecatrienoic acid" or "(7Z,10Z,13Z)-hexadeca-7,10,13-trienoic acid," as used herein, refers to

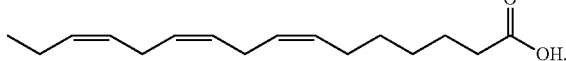

The term "eicosatrienoic acid" or "(11Z,14Z,17Z)-icosa-11,14,17-trienoic acid," as used herein, refers to

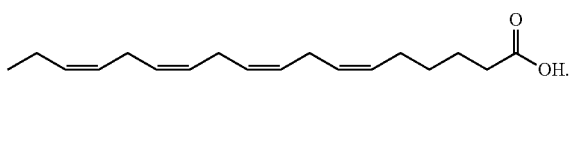 [SMILES: CC/C=C\C/C=C\C/C=C\C/C=C\CCCCC(=O)O]

The term "stearidonic acid" or "(6Z,9Z,12Z,15Z)-octadeca-6,9,12,15-tetraenoic acid," as used herein, refers to

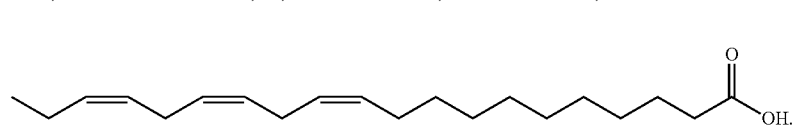

The term "eicosatetraenoic acid" or "(5Z,8Z,11Z,14Z,17Z)-icosa-5,8,11,14,17-pentaenoic acid," as used herein, refers to

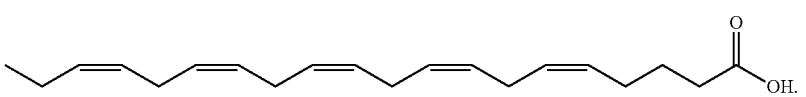 [SMILES: CC/C=C\C/C=C\C/C=C\C/C=C\C/C=C\CCCC(=O)O]

The term "heneicosapentaenoic acid" or "(6Z,9Z,12Z,15Z,18Z)-henicosa-6,9,12,15,18-pentaenoic acid," as used herein, refers to

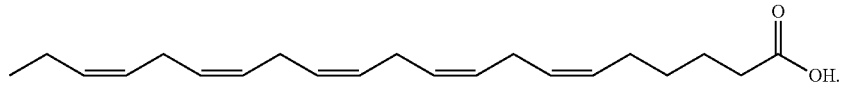

The term "clupanodonic acid" or "(7Z,10Z,13Z,16Z,19Z)-docosa-7,10,13,16,19-pentaenoic acid," as used herein, refers to

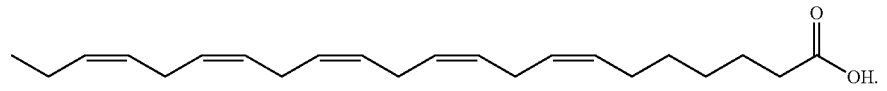 [SMILES: CC/C=C\C/C=C\C/C=C\C/C=C\C/C=C\CCCCCC(=O)O]

The term "osbond acid" or "(4Z,7Z,10Z,13Z,16Z)-docosa-4,7,10,13,16-pentaenoic acid," as used herein, refers to

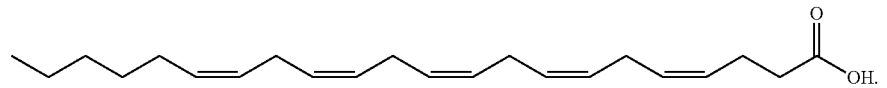 [SMILES: CCCCC/C=C\C/C=C\C/C=C\C/C=C\C/C=C\CCC(=O)O]

The term "(9Z,12Z,15Z,18Z,21Z)-tetracosa-9,12,15,18,21-pentaenoic acid," as used herein, refers to

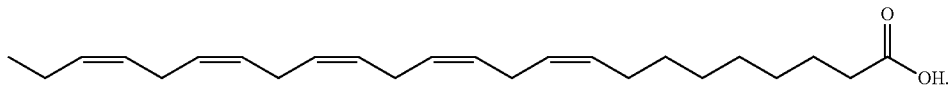

The term "nisinic acid" or "(6Z,9Z,12Z,15Z,18Z,21Z)-tetracosa-6,9,12,15,18,21-hexaenoic acid," as used herein, refers to

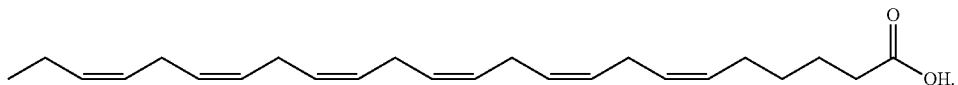

The term "γ-linolenic acid" or "(6Z,9Z,12Z)-octadeca-6,9,12-trienoic acid," as used herein, refers to

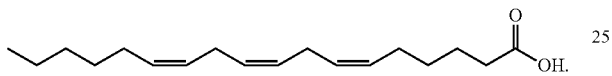

The term "eicosadienoic acid" or "(11Z,14Z)-icosa-11,14-dienoic acid," as used herein, refers to

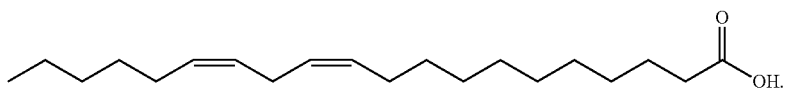 [SMILES: CCCCC/C=C\C/C=C\CCCCCCCCCC(=O)O]

The term "dihomo-γ-linolenic acid" or "(8Z,11Z,14Z)-icosa-8,11,14-trienoic acid," as used herein, refers to

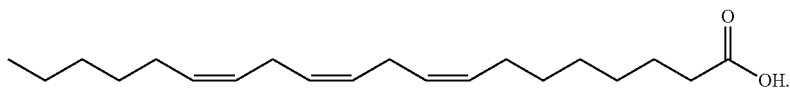 [SMILES: CCCCC/C=C\C/C=C\C/C=C\CCCCCCC(=O)O]

The term "docosadienoic acid" or "(13Z,16Z)-docosa-13,16-dienoic acid," as used herein, refers to

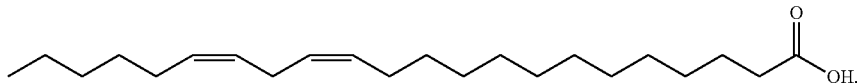 [SMILES: CCCCC/C=C\C/C=C\CCCCCCCCCCCC(=O)O]

The term "adrenic acid" or "(7Z,10Z,13Z,16Z)-docosa-7,10,13,16-tetraenoic acid," as used herein, refers to

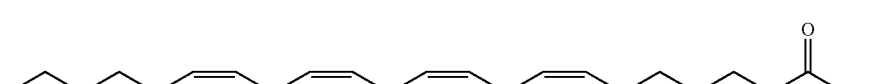

The term "tetracosatetraenoic acid" or "(9Z,12Z,15Z,18Z)-tetracosa-9,12,15,18-tetraenoic acid," as used herein, refers to

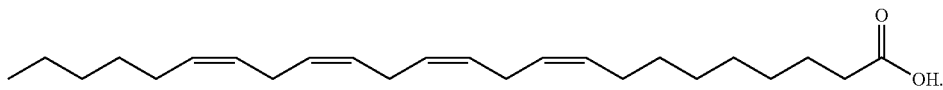 [SMILES: CCCCC/C=C\C/C=C\C/C=C\C/C=C\CCCCCCCC(=O)O]

The term "(6Z,9Z,12Z,15Z,18Z)-tetracosa-6,9,12,15,18-pentaenoic acid," as used herein, refers to

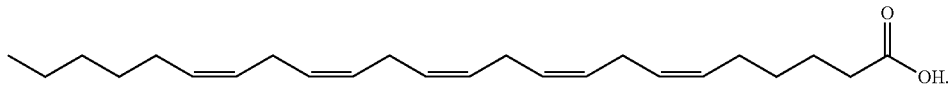 [SMILES: CCCCC/C=C\C/C=C\C/C=C\C/C=C\C/C=C\CCCCC(=O)O]

The term "(Z)-Eicos-11-enoic acid" or "(Z)-icos-11-enoic acid," as used herein, refers to

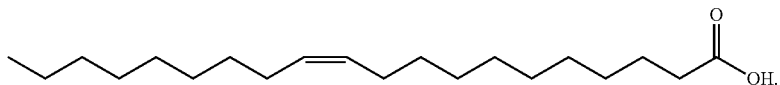 [SMILES: CCCCCCCC/C=C\CCCCCCCCCC(=O)O]

The term "paullinic acid" or "(Z)-icos-13-enoic acid," as used herein, refers to

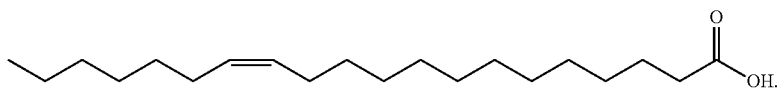 [SMILES: CCCCCC/C=C\CCCCCCCCCCCC(=O)O]

The term "mead acid" or "(5Z,8Z,11Z)-Eicosa-5,8,11-trienoic acid," as used herein, refers to

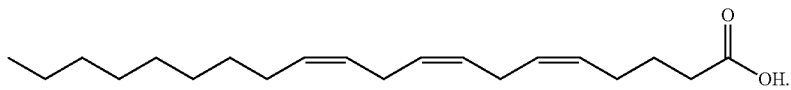 [SMILES: CCCCCCCC/C=C\C/C=C\C/C=C\CCCC(=O)O]

The term "nervonic acid," or "(Z)-tetracos-15-enoic acid," as used herein, refers to

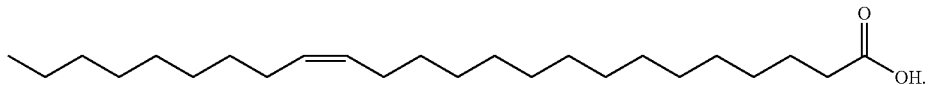 [SMILES: CCCCCCCC/C=C\CCCCCCCCCCCCCC(=O)O]

The term "rumenic acid" or "(9Z,11E)-octadeca-9,11-dienoic acid," as used herein, refers to

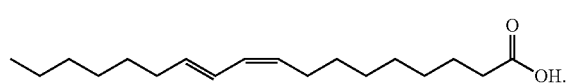 [SMILES: CCCCCC/C=C/C=C\CCCCCCCC(=O)O]

The term "α-calendic acid" or "(8E,10E,12Z)-octadeca-8,10,12-trienoic acid," as used herein, refers to The term "β-calendic acid" or "(8E,10E,12E)-octadeca-8,10,12-trienoic acid," as used herein, refers to

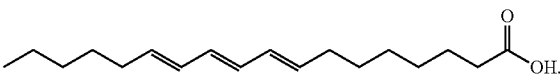 [SMILES: CCCCC/C=C/C=C/C=C/CCCCCCC(=O)O]

The term "jacaric acid" or "(8E,10Z,12E)-octadeca-8,10,12-trienoic acid,"

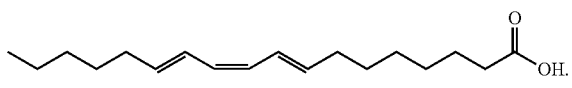 [SMILES: CCCCC/C=C/C=C\C=C\CCCCCCC(=O)O]

The term "α-eleostearic acid" or "(9Z,11E,13E)-octadeca-9,11,13-trienoic acid," as used herein, refers to

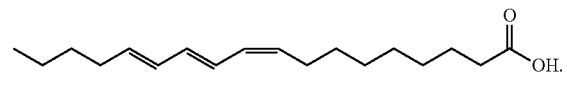 [SMILES: CCCC/C=C/C=C/C=C\CCCCCCCC(=O)O]

The term "β-eleostearic acid" or "(9E,11E,13E)-octadeca-9,11,13-trienoic acid," as used herein, refers to

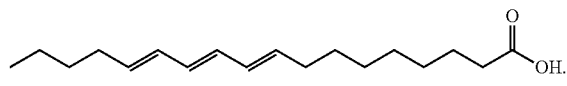 [SMILES: CCCC/C=C/C=C/C=C/CCCCCCCC(=O)O]

The term "catalpic acid" or "(9E,11E,13Z)-octadeca-9,11,13-trienoic acid," as used herein, refers to

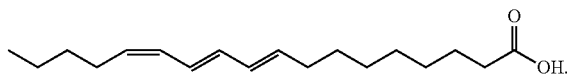 [SMILES: CCCC\C=C/C=C/C=C/CCCCCCCC(=O)O]

The term "punicic acid" or "(9Z,11E,13Z)-octadeca-9,11,13-trienoic acid," as used herein, refers to

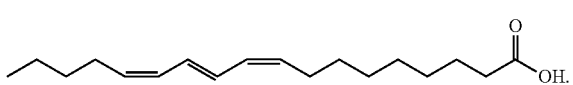 [SMILES: CCCC\C=C/C=C/C=C\CCCCCCCC(=O)O]

The term "rumelenic acid" or "(9E,11Z,15E)-octadeca-9,11,15-trienoic acid," as used herein, refers to

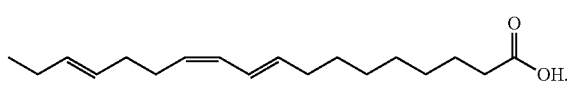

The term "α-parinaric acid" or "(9Z,11E,13E,15Z)-octadeca-9,11,13,15-tetraenoic acid," as used herein, refers to

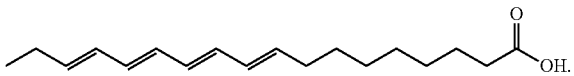 [SMILES: CC/C=C/C=C/C=C/C=C/CCCCCCCC(=O)O]

The term "β-parinaric acid" or "(9E,11E,13E,15E)-octadeca-9,11,13,15-tetraenoic acid," as used herein, refers to

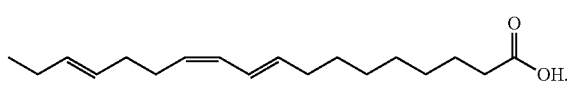

The term "bosseopentaenoic acid" or "(5Z,8Z,10E,12E,14Z)-icosa-5,8,10,12,14-pentaenoic acid," as used herein, refers to

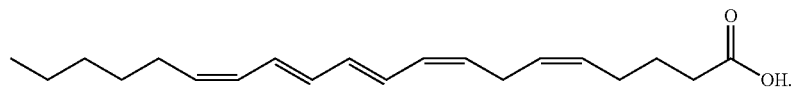 [SMILES: CCCCC\C=C/C=C/C=C/C=C\C/C=C\CCCC(=O)O]

The term "pinolenic acid" or "(5Z,9Z,12Z)-octadeca-5,9,12-trienoic acid," as used herein, refers to

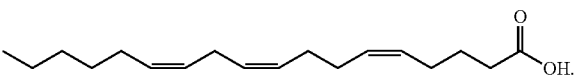 [SMILES: CCCCC/C=C\C/C=C\CC/C=C\CCCC(=O)O]

The term "podocarpic acid" or "(5Z,11Z,14Z)-icosa-5,11,14-trienoic acid," as used herein, refers to

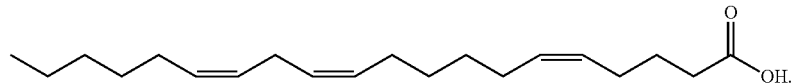

The term "propionic acid," as used herein, refers to $CH_3CH_2COOH$.

The term "butyric acid," as used herein, refers to $CH_3(CH_2)_2COOH$.

The term "valeric acid," as used herein, refers to $CH_3(CH_2)_3COOH$.

The term "caproic acid," as used herein, refers to $CH_3(CH_2)_4COOH$.

The term "enanthic acid," as used herein, refers to $CH_3(CH_2)_5COOH$.

The term "caprylic acid," as used herein, refers to $CH_3(CH_2)_6COOH$.

The term "pelargonic acid," as used herein, refers to $CH_3(CH_2)_7COOH$.

The term "capric acid," as used herein, refers to $CH_3(CH_2)_8COOH$.

The term "undecylic acid," as used herein, refers to $CH_3(CH_2)_9COOH$.

The term "lauric acid," as used herein, refers to $CH_3(CH_2)_{10}COOH$.

The term "tridecylic acid," as used herein, refers to $CH_3(CH_2)_{11}COOH$.

The term "myristic acid," as used herein, refers to $CH_3(CH_2)_{12}COOH$.

The term "pentadecylic acid," as used herein, refers to $CH_3(CH_2)_{13}COOH$.

The term "palmitic acid," as used herein, refers to $CH_3(CH_2)_{14}COOH$.

The term "margaric acid," as used herein, refers to $CH_3(CH_2)_{15}COOH$.

The term "stearic acid," as used herein, refers to $CH_3(CH_2)_{16}COOH$.

The term "nonadecylic acid," as used herein, refers to $CH_3(CH_2)_{17}COOH$.

The term "arachidic acid," as used herein, refers to $CH_3(CH_2)_{18}COOH$.

The term "heneicosylic acid," as used herein, refers to $CH_3(CH_2)_{19}COOH$.

The term "behenic acid," as used herein, refers to $CH_3(CH_2)_{20}COOH$.

The term "tricosylic acid," as used herein, refers to $CH_3(CH_2)_{21}COOH$.

The term "lignoceric acid," as used herein, refers to $CH_3(CH_2)_{22}COOH$.

The term "pentacosylic acid," as used herein, refers to $CH_3(CH_2)_{23}COOH$.

The term "cerotic acid," as used herein, refers to $CH_3(CH_2)_{24}COOH$.

The term "heptacosylic acid," as used herein, refers to $CH_3(CH_2)_{25}COOH$.

The term "montanic acid," as used herein, refers to $CH_3(CH_2)_{26}COOH$.

The term "nonacosylic acid," as used herein, refers to $CH_3(CH_2)_{27}COOH$.

The term "melissic acid," as used herein, refers to $CH_3(CH_2)_{28}COOH$.

The term "henatriacontylic acid," as used herein, refers to $CH_3(CH_2)_{29}COOH$.

The term "lacceroic acid," as used herein, refers to $CH_3(CH_2)_{30}COOH$.

The term "psyllic acid," as used herein, refers to $CH_3(CH_2)_{31}COOH$.

The term "geddic acid," as used herein, refers to $CH_3(CH_2)_{32}COOH$.

The term "ceroplastic acid," as used herein, refers to $CH_3(CH_2)_{33}COOH$.

The term "hexatriacontylic acid," as used herein, refers to $CH_3(CH_2)_{34}COOH$.

2. Compositions

The compositions disclosed herein include an imidazoline compound, a quaternary amine, and a phosphonium compound. The compositions can further include a demulsifer. The compositions can further include a synergist. The compositions can further include a solvent. The compositions can further include one or more additional components.

The composition can include an imidazoline compound, a quaternary amine, a phosphonium compound, and a demulsifier.

Further, the composition can include an imidazoline compound, a quaternary amine, a phosphonium compound, a demulsifier, and a synergist.

Additionally, the composition can include an imidazoline compound, a quaternary amine, a phosphonium compound, a demulsifier, and a solvent.

Yet further, the composition can include an imidazoline compound, a quaternary amine, a phosphonium compound, and a solvent.

Additionally, the composition can include an imidazoline compound, a quaternary amine, a phosphonium compound, a synergist, and a solvent.

Further, the composition can include an imidazoline compound, a quaternary amine, a phosphonium compound, a demulsifier, a synergist, and a solvent.

a. Imidazoline Compounds

The compositions disclosed herein include at least one imidazoline compound. The imidazoline compound can have formula (I), (II), or (III),

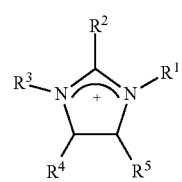

(I)

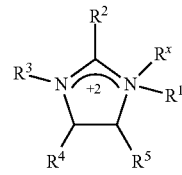

(II)

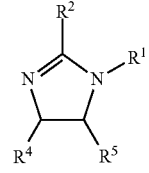

(III)

wherein $R^1$, $R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, —$COR^6$, —$CO_2R^7$, —$SO_3R^8$, —$PO_3H_2$, —$CON(R^9)(R^{10})$, —$OR^{11}$, and —$N(R^{12})(R^{13})$;

$R^2$ is a radical derived from a fatty acid;

$R^3$ and $Rx$ are each independently selected from a radical derived from an unsaturated acid;

$R^6$, $R^7$, $R^8$, $R^9$, $R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, —$COR^{14}$, —$CO_2R^{15}$, -alkyl-$COR^{16}$, and -alkyl-$CO_2R^{17}$; and $R^{14}$, $R^{15}$, $R^{16}$, and $R^{17}$ are each independently, at each occurrence, selected from hydrogen, alkyl, and alkenyl.

For these imidazolines, R groups of carboxylic acid moieties can be absent where the R=H and the carboxylic acid moiety is deprotonated. For example, $R^{15}$ and/or $R^{17}$ can be absent where the $R^{12}$ and/or $R^{13}$ is a deprotonated carboxylic acid moiety (e.g., where $R^{12}$ is —$CH_2CH_2CO_2^-$).

For an imidazoline compound, $R^1$ can be unsubstituted alkyl. For example, $R^1$ can be unsubstituted $C_1$-$C_{10}$-alkyl (e.g., methyl, ethyl, propyl (e.g., n-propyl, isopropyl), butyl (e.g., n-butyl, isobutyl, tert-butyl, sec-butyl), pentyl (e.g., n-pentyl, isopentyl, tert-pentyl, neopentyl, sec-pentyl, 3-pentyl), hexyl, heptyl, octyl, nonyl, or decyl). Further, $R^1$ can be unsubstituted $C_2$-$C_{10}$-alkyl. For these imidazoline compounds, $R^1$ can be unsubstituted $C_2$-$C_8$-alkyl. Further, $R^1$ can be unsubstituted $C_2$-$C_6$-alkyl. Preferably, $R^1$ is propyl, butyl, or hexyl.

For these imidazolines, $R^1$ is substituted alkyl. For example, $R^1$ is substituted $C_1$-$C_{10}$-alkyl, substituted $C_2$-$C_{10}$-alkyl, substituted $C_2$-$C_8$-alkyl, or substituted $C_2$-$C_6$-alkyl. Further, $R^1$ is $C_1$-$C_{10}$-alkyl, $C_2$-$C_{10}$-alkyl, $C_2$-$C_8$-alkyl, or $C_2$-$C_6$-alkyl, substituted with one substituent selected from —$COR^6$, —$CO_2R^7$, —$SO_3R^8$, —$PO_3H_2$, —$CON(R^9)(R^{10})$, —$OR^{11}$, and —$N(R^{12})(R^{13})$, wherein $R^6$, $R^7$, $R^8$, $R^9$, $R^{10}$, $R^{11}$, $R^{12}$, and $R^{13}$ are as defined above. More specifically, $R^1$ is $C_2$-$C_6$-alkyl, substituted with one substituent selected from —$N(R^{12})(R^{13})$, wherein $R^{12}$ and $R^{13}$ are each independently selected from hydrogen, alkyl, —$COR^{14}$, —$CO_2R^{15}$, -alkyl-$COR^{16}$, and -alkyl-$CO_2R^{17}$, wherein $R^{14}$, $R^{15}$, $R^{16}$, and $R^{17}$ are as defined above. Further, $R^1$ is $C_2$-$C_6$-alkyl, substituted with one substituent selected from —$N(R^{12})(R^{13})$, wherein $R^{12}$ and $R^{13}$ are each independently selected from hydrogen, $C_2$-$C_6$-alkyl, —$COR^{14}$, —$CO_2R^{15}$, —$C_2$-$C_6$-alkyl-$COR^{16}$, and —$C_2$-$C_6$-alkyl-$CO_2R^{17}$, wherein $R^{14}$, $R^{15}$, $R^{16}$, and $R^{17}$ are selected from hydrogen and $C_1$-$C_{34}$-alkyl. For these imidazolines, $R^1$ is linear $C_2$-$C_6$-alkyl, substituted with one substituent that is a terminal —$N(R^{12})(R^{13})$, wherein $R^{12}$ and $R^{13}$ are each independently selected from hydrogen, —$COR^{14}$, —$CO_2R^{15}$, —$C_2$-$C_6$-alkyl-$COR^{16}$, and —$C_2$-$C_6$-alkyl-$CO_2R^{17}$, wherein $R^{14}$, $R^{15}$, $R^{16}$, and $R^{17}$ are selected from hydrogen and $C_1$-$C_{34}$-alkyl. For example, $R^1$ is linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_{17}H_{33}$, or —$C_{17}H_{31}$. Further, $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen.

For the imidazolines of formulae (I), (II), and (III), $R^2$ is $C_4$-$C_{34}$-alkyl or $C_4$-$C_{34}$-alkenyl. For example, $R^2$ is —$(CH_2)_3CH_3$; —$(CH_2)_4CH_3$; —$(CH_2)_5CH_3$; —$(CH_2)_6CH_3$; —$(CH_2)_7CH_3$; —$(CH_2)_8CH_3$; —$(CH_2)_9CH_3$; —$(CH_2)_{10}CH_3$; —$(CH_2)_{11}CH_3$; —$(CH_2)_{12}CH_3$; —$(CH_2)_{13}CH_3$; —$(CH_2)_{14}CH_3$; —$(CH_2)_{15}CH_3$; —$(CH_2)_{16}CH_3$; —$(CH_2)_{17}CH_3$; —$(CH_2)_{18}CH_3$; —$(CH_2)_{19}CH_3$; —$(CH_2)_{20}CH_3$; —$(CH_2)_{21}CH_3$; —$(CH_2)_{22}CH_3$; —$(CH_2)_{23}CH_3$; —$(CH_2)_{24}CH_3$; —$(CH_2)_{25}CH_3$; —$(CH_2)_{26}CH_3$; —$(CH_2)_{27}CH_3$; —$(CH_2)_{28}CH_3$; —$(CH_2)_{29}CH_3$; —$(CH_2)_{30}CH_3$; —$(CH_2)_{31}CH_3$; —$(CH_2)_{32}CH_3$; —$(CH_2)_{33}CH_3$; —$(CH_2)_{34}CH_3$; —$(CH_2)_2CH=CHCH_2CH=CHCH_2CH=CHCH_2CH=CH(CH_2)_4CH_3$; —$(CH_2)_2CH=CHCH_2CH=CHCH_2CH=CHCH_2CH=CHCH_2CH_3$; —$(CH_2)_3CH=CHCH_2CH=CHCH_2CH=CH(CH_2)_7CH_3$; —$(CH_2)_3CH=CHCH_2CH_2CH=CHCH_2CH=CH(CH_2)_4CH_3$; —$(CH_2)_3CH=CH(CH_2)_4CH=CHCH_2CH=CH(CH_2)_4CH_3$; —$(CH_2)_3CH=CHCH_2CH=CHCH_2CH=CHCH_2CH=CH(CH_2)_4CH_3$; —$(CH_2)_3CH=CHCH_2CH=CHCH_2CH=CHCH_2CH=CHCH_2CH_3$; —$(CH_2)_3CH=CH=CH=CH=CH=CH(CH_2)_4CH_3$; —$(CH_2)_4CH=CH(CH_2)_8CH_3$; —$(CH_2)_4CH=CHCH_2CH=CHCH_2CH=CH(CH_2)_4CH_3$; —$(CH_2)_4CH=CHCH_2CH=CHCH_2CH=CHCH_2CH=CHCH_2CH_3$; —$(CH_2)_4CH=CHCH_2CH=CHCH_2CH=CHCH_2CH=CHCH_2CH=CHCH_2CH_3$; —$(CH_2)_4CH=CHCH_2CH=CHCH_2CH=CH(CH_2)_4CH_3$; —$(CH_2)_4CH=CHCH_2CH=CHCH_2CH=CHCH_2CH=CHCH_2CH=CHCH_2CH_3$; —$(CH_2)_5CH=CHCH_2CH=CHCH_2CH=CHCH_2CH_3$; —$(CH_2)_5CH=CHCH_2CH=CHCH_2CH=CH(CH_2)_4CH_3$; —$(CH_2)_5CH=CHCH_2CH=CHCH_2CH=CHCH_2CH=CHCH_2$; —$(CH_2)_6CH=CHCH=CHCH=CH$ —$(CH_2)_4CH_3$; —$(CH_2)_6CH=CHCH_2CH=CHCH_2$ $CH=CHCH_2CH=CH(CH_2)_4CH_3$; —$(CH_2)_7CH=CH$ $(CH_2)_3CH_3$; —$(CH_2)_7CH=CH(CH_2)_5CH_3$; —$(CH_2)_7$ $CH=CH(CH_2)_7CH_3$; —$(CH_2)_7CH=CHCH=$ $CHCH=CH(CH_2)_3CH_3$; —$(CH_2)_7CH=CHCH=CH$ $(CH_2)_5CH_3$; —$(CH_2)_7CH=CHCH_2CH=CH(CH_2)_4CH_3$; —$(CH_2)_7CH=CHCH_2CH=CH(CH_2)_4CH_3$; —$(CH_2)_7$ $CH=CHCH=CHCH_2CH_2CH=CHCH_2CH_3$; —$(CH_2)_7$ $CH=CHCH=CHCH=CHCH=CHCH_2CH_3$; —$(CH_2)_7$ $CH=CHCH_2CH=CHCH_2CH=CHCH_2CH=CH(CH_2)_4$ $CH_3$; —$(CH_2)_7CH=CHCH_2CH=CHCH_2CH=$ $CHCH_2CH_3$; —$(CH_2)_7CH=CHCH_2CH=CHCH_2$ $CH=CHCH_2$ $CH=CHCH_2$ $CH=CHCH_2CH_3$; —$(CH_2)_9$ $CH=CH(CH_2)_5CH_3$; —$(CH_2)_9CH=CHCH_2CH=CH$ $(CH_2)_4CH_3$; —$(CH_2)_9CH=CHCH_2CH=CHCH_2$ $CH=CHCH_2CH_3$; —$(CH_2)_9CH=CH(CH_2)_7CH_3$; —$(CH_2)_{11}CH=CH(CH_2)_5CH_3$; —$(CH_2)_{11}CH=CH(CH_2)_7$ $CH_3$; —$(CH_2)_{11}CH=CHCH_2CH=CH(CH_2)_4CH_3$; or —$(CH_2)_{13}CH=CH(CH_2)_7CH_3$.

For the imidazolines, $R^2$ can be a radical derived from a saturated or unsaturated fatty acid. Suitable saturated fatty acids include, but are not limited to, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, and hexatriacontylic acid. Suitable unsaturated fatty acids include, but are not limited to, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, hexadecatrienoic acid, stearidonic acid, eicosatrienoic acid, eicosatetraenoic acid, heneicosapentaenoic acid, clupanodonic acid, osbond acid, (9Z,12Z,15Z,18Z,21Z)-tetracosa-9,12,15,18,21-pentaenoic acid, nisinic acid, γ-linolenic acid, eicosadienoic acid, dihomo-γ-linolenic acid, docosadienoic acid, adrenic acid, tetracosatetraenoic acid, (6Z,9Z, 12Z,15Z,18Z)-tetracosa-6,9,12,15,18-pentaenoic acid, (Z)-Eicos-11-enoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, and podocarpic acid. Preferably, $R^2$ is derived from coconut oil, beef tallow, or tall oil fatty acids (TOFA).

For the imidazoline, $R^3$ is —$C(R^aR^b)$—$C(R^cR^d)$—$CO_2R^e$, wherein $R^a$, $R^b$, $R^c$, and $R^d$ are each independently selected from the group consisting of hydrogen (—H), halogen, and alkyl, and wherein $R^e$ is hydrogen (—H) or alkyl. For example, $R^3$ is —$C(R^aR^b)$—$C(R^cR^d)$—$CO_2R^e$, wherein $R^a$, $R^b$, $R^c$, and $R^d$ are each independently selected from the group consisting of hydrogen (—H), halogen, and $C_1$-$C_6$-alkyl, and wherein $R^e$ is hydrogen (—H) or $C_1$-$C_6$-alkyl. Further, $R^3$ is —$CH_2CH_2CO_2R^e$, wherein $R^e$ is hydrogen (—H) or $C_1$-$C_6$-alkyl. Additionally, $R^e$ can be absent where the $R^3$ is a deprotonated carboxylic acid moiety (e.g., where $R^3$ is —$CH_2CH_2CO_2^-$).

For the imidazolines, $R^3$ can be derived from an acrylic acid. Suitable acrylic acids include, but are not limited to, acrylic acid, methacrylic acid, 2-ethylacrylic acid, 2-propylacrylic acid, and 2-(trifluoromethyl)acrylic acid. For example, $R^3$ can be derived from acrylic acid ($H_2C=CHCO_2H$).

Imidazolines of formulae (I), (II), or (III) can have $R^x$ is —$C(R^aR^b)$—$C(R^cR^d)$—$CO_2R^e$, wherein $R^a$, $R^b$, $R^c$, and $R^d$ are each independently selected from the group consisting of hydrogen (—H), halogen, and alkyl, and wherein $R^e$ is hydrogen (—H) or alkyl. Further, $R^x$ can be —$C(R^aR^b)$—$C(R^cR^d)$—$CO_2R^e$, wherein $R^a$, $R^b$, $R^c$, and $R^d$ are each independently selected from the group consisting of hydrogen (—H), halogen, and $C_1$-$C_6$-alkyl, and wherein $R^e$ is hydrogen (—H) or $C_1$-$C_6$-alkyl. Additionally, $R^x$ is —$CH_2CH_2CO_2R^e$, wherein $R^e$ is hydrogen (—H) or $C_1$-$C_6$-alkyl. Further, $R^e$ can be absent where the $R^x$ is a deprotonated carboxylic acid moiety (e.g., where $R^x$ is —$CH_2CH_2CO_2^-$).

For the imidazolines described herein, $R^x$ can be derived from an acrylic acid. Suitable acrylic acids include, but are not limited to, acrylic acid, methacrylic acid, 2-ethylacrylic acid, 2-propylacrylic acid, and 2-(trifluoromethyl)acrylic acid. For example, $R^x$ can be derived from acrylic acid ($H_2C=CHCO_2H$).

Imidazolines of formulae (I), (II), or (III) can have $R^4$ and $R^5$ each independently be an unsubstituted $C_1$-$C_{10}$-alkyl (e.g., methyl, ethyl, propyl (e.g., n-propyl, isopropyl), butyl (e.g., n-butyl, isobutyl, tert-butyl, sec-butyl), pentyl (e.g., n-pentyl, isopentyl, tert-pentyl, neopentyl, sec-pentyl, 3-pentyl), hexyl, heptyl, octyl, nonyl, or decyl) or hydrogen. Further, $R^4$ and $R^5$ can each independently be an unsubstituted $C_1$-$C_6$ alkyl group or hydrogen. Preferably, $R^4$ and $R^5$ are each hydrogen (—H).

Imidazolines of formulae (I), (II), or (III) can have $R^6$, $R^7$, $R^8$, $R^9$, $R^{10}$, and $R^{11}$ each independently be, at each occurrence, selected from hydrogen, unsubstituted alkyl, and unsubstituted alkenyl. For example, $R^6$, $R^7$, $R^8$, $R^9$, $R^{10}$, and $R^{11}$ can each independently be, at each occurrence, selected from hydrogen, unsubstituted $C_1$-$C_{34}$-alkyl, and unsubstituted $C_2$-$C_{34}$-alkenyl. Further, $R^6$, $R^7$, $R^8$, $R^9$, $R^{10}$, and $R^{11}$ can each independently be, at each occurrence, selected from hydrogen, unsubstituted $C_1$-$C_{10}$-alkyl, and unsubstituted $C_2$-$C_{10}$-alkenyl.

Further, $R^6$, $R^7$, $R^8$, $R^9$, $R^{10}$, and $R^{11}$ can each independently be, at each occurrence, selected from hydrogen, and a radical derived from a fatty acid.

For the imidazoline compounds, $R^{12}$ and $R^{13}$ can each independently be, at each occurrence, selected from hydrogen, $C_1$-$C_{10}$-alkyl, —$COR^{14}$, —$CO_2R^{15}$, —$C_1$-$C_{10}$-alkyl-$COR^{16}$, and —$C_1$-$C_{10}$-alkyl-$CO_2R^{17}$. Further, $R^{12}$ and $R^{13}$ can each independently be, at each occurrence, selected from hydrogen, unsubstituted $C_1$-$C_{10}$-alkyl, —$COR^{14}$, —$CO_2R^{15}$, —$C_1$-$C_{10}$-alkyl-$COR^{16}$, and —$C_1$-$C_{10}$-alkyl-$CO_2R^{17}$.

For the imidazolines, $R^{14}$, $R^{15}$, $R^{16}$, and $R^{17}$ can each independently be, at each occurrence, selected from hydrogen, unsubstituted alkyl, and unsubstituted alkenyl. Further, $R^{14}$, $R^{15}$, $R^{16}$, and $R^{17}$ can each independently be, at each occurrence, selected from hydrogen, unsubstituted $C_1$-$C_{34}$-alkyl, and unsubstituted $C_2$-$C_{34}$-alkenyl. Additionally, $R^{14}$, $R^{15}$, $R^{16}$, and $R^{17}$ can each independently be, at each occurrence, selected from hydrogen, unsubstituted $C_1$-$C_{10}$-alkyl, and unsubstituted $C_2$-$C_{10}$-alkenyl. Further, $R^{15}$ and/or $R^{17}$ can be absent where the carboxylic acid moiety is deprotonated.

Imidazoline compounds can have $R^{14}$, $R^{15}$, $R^{16}$, and $R^{17}$ each independently be, at each occurrence, selected from hydrogen, and a radical derived from a fatty acid. Further, $R^{14}$, $R^{15}$, $R^{16}$, and $R^{17}$ can each independently be, at each occurrence, selected from hydrogen, $C_4$-$C_{34}$-alkyl, and $C_4$-$C_{34}$-alkenyl. Additionally, $R^{14}$, $R^{15}$, $R^{16}$, and $R^{17}$ can each independently be, at each occurrence, selected from hydrogen; —$(CH_2)_3CH_3$; —$(CH_2)_4CH_3$; —$(CH_2)_5CH_3$; —$(CH_2)_6CH_3$; —$(CH_2)_7CH_3$; —$(CH_2)_8CH_3$; —$(CH_2)_9CH_3$; —$(CH_2)_{10}CH_3$; —$(CH_2)_{11}CH_3$; —$(CH_2)_{12}CH_3$; —$(CH_2)_{13}CH_3$; —$(CH_2)_{14}CH_3$; —$(CH_2)_{15}CH_3$; —$(CH_2)_{16}CH_3$; —$(CH_2)_{17}CH_3$; —$(CH_2)_{18}CH_3$; —$(CH_2)_{19}CH_3$; —$(CH_2)_{20}CH_3$; —$(CH_2)_{21}CH_3$; —$(CH_2)_{22}CH_3$; —$(CH_2)_{23}CH_3$; —$(CH_2)_{24}CH_3$; —$(CH_2)_{25}CH_3$; —$(CH_2)_{26}CH_3$; —$(CH_2)_{27}CH_3$; —$(CH_2)_{28}CH_3$; —$(CH_2)_{29}CH_3$; —$(CH_2)_{30}CH_3$; —$(CH_2)_{31}CH_3$; —$(CH_2)_{32}CH_3$; —$(CH_2)_{33}CH_3$; —$(CH_2)_{34}CH_3$; —$(CH_2)_2CH=CHCH_2CH=CHCH_2CH=CHCH_2CH=CH(CH_2)_4CH_3$; —$(CH_2)_2CH=CHCH_2CH=CHCH_2CH=CHCH_2CH=CHCH_2CH=CHCH_2CH=CHCH_2CH_3$; —$(CH_2)_3CH=CHCH_2CH=CHCH_2CH=CH(CH_2)_7CH_3$; —$(CH_2)_3CH=CHCH_2CH_2CH=CHCH_2CH=CH(CH_2)_4CH_3$; —$(CH_2)_3CH=CH(CH_2)_4CH=CHCH_2CH=CH(CH_2)_4CH_3$; —$(CH_2)_3CH=CHCH_2CH=CHCH_2CH=CHCH_2CH=CH(CH_2)_4CH_3$; —$(CH_2)_3CH=CHCH_2CH=CHCH_2CH=CHCH_2CH=CHCH_2CH=CHCH_2CH_3$; —$(CH_2)_3CH=CHCH=CHCH=CHCH=CH(CH_2)_4CH_3$; —$(CH_2)_4CH=CH(CH_2)_8CH_3$; —$(CH_2)_4CH=CHCH_2CH=CHCH_2CH=CH(CH_2)_4CH_3$; —$(CH_2)_4CH=CHCH_2CH=CHCH_2CH=CHCH_2CH=CHCH_2CH_3$; —$(CH_2)_4CH=CHCH_2CH=CHCH_2CH=CHCH_2CH=CHCH_2CH=CHCH_2CH_3$; —$(CH_2)_4CH=CHCH_2CH=CHCH_2CH=CH(CH_2)_4CH_3$; —$(CH_2)_4CH=CHCH_2CH=CHCH_2CH=CHCH_2CH=CHCH_2CH=CHCH_2CH_3$; —$(CH_2)_5CH=CHCH_2CH=CHCH_2CH=CHCH_2CH_3$; —$(CH_2)_5CH=CHCH_2CH=CHCH_2CH=CH(CH_2)_4CH_3$; —$(CH_2)_5CH=CHCH_2CH=CHCH_2CH=CHCH_2CH=CHCH_2CH_3$; —$(CH_2)_6CH=CHCH=CHCH=CH(CH_2)_4CH_3$; —$(CH_2)_6CH=CHCH_2CH=CHCH_2CH=CH(CH_2)_4CH_3$; —$(CH_2)_7CH=CH(CH_2)_3CH_3$; —$(CH_2)_7CH=CH(CH_2)_5CH_3$; —$(CH_2)_7CH=CH(CH_2)_7CH_3$; —$(CH_2)_7CH=CHCH=CHCH=CH(CH_2)_3CH_3$; —$(CH_2)_7CH=CHCH=CH(CH_2)_5CH_3$; —$(CH_2)_7CH=CHCH_2CH=CH(CH_2)_4CH_3$; —$(CH_2)_7CH=CHCH_2CH=CH(CH_2)_4CH_3$; —$(CH_2)_7CH=CHCH_2CH_2CH=CHCH_2CH_3$; —$(CH_2)_7CH=CHCH=CHCH=CHCH_2CH_3$; —$(CH_2)_7CH=CHCH_2CH=CHCH_2CH=CHCH_2CH=CH(CH_2)_4CH_3$; —$(CH_2)_7CH=CHCH_2CH_3$; —$(CH_2)_7CH=CHCH_2CH=CHCH_2CH=CHCH_2CH=CHCH_2CH_3$; —$(CH_2)_9CH=CH(CH_2)_5CH_3$; —$(CH_2)_9CH=CHCH_2CH=CH(CH_2)_4CH_3$; —$(CH_2)_9CH=CHCH_2CH=CHCH_2CH=CHCH_2CH_3$; —$(CH_2)_9CH=CH(CH_2)_7CH_3$; —$(CH_2)_{11}CH=CH(CH_2)_5CH_3$; —$(CH_2)_{11}CH=CH(CH_2)_7CH_3$; —$(CH_2)_{11}CH=CHCH_2CH=CH(CH_2)_4CH_3$; and —$(CH_2)_{13}CH=CH(CH_2)_7CH_3$.

For the imidazolines of formulae (I), (II), and (III), $R^{14}$, $R^{15}$, $R^{16}$, and $R^{17}$ can each independently be, at each occurrence, selected from hydrogen, a radical derived from a saturated fatty acid, and a radical derived from an unsaturated fatty acid. Suitable saturated fatty acids include, but are not limited to, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, and hexatriacontylic acid. Suitable unsaturated fatty acids include, but are not limited to, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, hexadecatrienoic acid, stearidonic acid, eicosatrienoic acid, eicosatetraenoic acid, heneicosapentaenoic acid, clupanodonic acid, osbond acid, (9Z,12Z,15Z,18Z,21Z)-tetracosa-9,12,15,18,21-pentaenoic acid, nisinic acid, γ-linolenic acid, eicosadienoic acid, dihomo-γ-linolenic acid, docosadienoic acid, adrenic acid, tetracosatetraenoic acid, (6Z,9Z,12Z,15Z,18Z)-tetracosa-6,9,12,15,18-pentaenoic acid, (Z)-Eicos-11-enoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, and podocarpic acid. Further, $R^{14}$, $R^{15}$, $R^{16}$, and $R^{17}$ are each independently, at each occurrence, hydrogen or a radical derived from coconut oil, beef tallow, or tall oil fatty acids (TOFA).

Preferably, the imidazoline is a compound of formula (I), wherein $R^1$ is unsubstituted $C_2$-$C_6$-alkyl; $R^2$ is —$C_{17}H_{35}$, —$C_{17}H_{33}$, or —$C_{17}H_{31}$; $R^3$ is —$CH_2CH_2CO_2R^e$, wherein Re is hydrogen (—H), $C_1$-$C_6$-alkyl, or $R^e$ is absent (e.g., $R^3$ is —$CH_2CH_2CO_2^-$); $R^4$ is hydrogen; and $R^5$ is hydrogen.

Alternatively, the imidazoline is a compound of formula (I), wherein $R^1$ is linear $C_2$-alkyl, substituted with one substituent that is a terminal —$N(R^{12})(R^{13})$, wherein $R^{12}$ is hydrogen and $R^{13}$ is —$COR^{14}$ wherein $R^{14}$ is —$C_{17}H_{35}$, —$C_{17}H_{33}$, or —$C_{17}H_{31}$; $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen (—H), $C_1$-$C_6$-alkyl, or $R^e$ is absent (e.g., $R^3$ is —$CH_2CH_2CO_2^-$); $R^4$ is hydrogen; and $R^5$ is hydrogen.

Further, the imidazoline is a compound of formula (I), wherein $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or is absent (e.g., $R^{12}$ is —$C_2$-alkyl-$CO_2^-$); $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen (—H), $C_1$-$C_6$-alkyl, or $R^e$ is absent (e.g., $R^3$ is —$CH_2CH_2CO_2^-$); $R^4$ is hydrogen; and $R^5$ is hydrogen.

Additionally, the imidazoline is a compound of formula (II), wherein $R^1$ is unsubstituted $C_2$-$C_6$-alkyl; $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen (—H), $C_1$-$C_6$-alkyl, or $R^e$ is absent (e.g., $R^3$ is —$CH_2CH_2CO_2^-$); $R^x$ is —$CH_2CH_2CO_2R^e$, wherein $R^e$ is hydrogen (—H), $C_1$-$C_6$-alkyl, or $R^e$ is absent (e.g., $R^x$ is —$CH_2CH_2CO_2^-$); $R^4$ is hydrogen; and $R^5$ is hydrogen.

The imidazoline can be a compound of formula (II), wherein $R^1$ is linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_{17}H_{33}$, or —$C_{17}H_{31}$; $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen (—H), $C_1$-$C_6$-alkyl, or $R^e$ is absent (e.g., $R^3$ is —$CH_2CH_2CO_2^-$); $R^x$ is —$CH_2CH_2CO_2R^e$, wherein $R^e$ is hydrogen (—H), $C_1$-$C_6$-alkyl, or $R^e$ is absent (e.g., $R^x$ is —$CH_2CH_2CO_2^-$); $R^4$ is hydrogen; and $R^5$ is hydrogen.

The imidazoline can be a compound of formula (II), wherein $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or is absent (e.g., $R^{12}$ is —$C_2$-alkyl-$CO_2^-$); $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen (—H), $C_1$-$C_6$-alkyl, or $R^e$ is absent (e.g., $R^3$ is —$CH_2CH_2CO_2^-$); $R^x$ is —$CH_2CH_2CO_2R^e$, wherein $R^e$ is hydrogen (—H), $C_1$-$C_6$-alkyl, or $R^e$ is absent (e.g., $R^x$ is —$CH_2CH_2CO_2^-$); $R^4$ is hydrogen; and $R^5$ is hydrogen.

The imidazoline can be a compound of formula (III), wherein $R^1$ is unsubstituted $C_2$-$C_6$-alkyl; $R^2$ is —$C_{17}H_{35}$, —$C_{17}H_{33}$, or —$C_{17}H_{31}$; $R^4$ is hydrogen; and $R^5$ is hydrogen.

The imidazoline can be a compound of formula (III), wherein $R^1$ is linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_{17}H_{33}$, or —$C_{17}H_{31}$; $R^2$ is —$C_{17}H_{35}$, —$C_{17}H_{33}$, or —$C_{17}H_{31}$; $R^4$ is hydrogen; and $R^5$ is hydrogen.

The imidazoline can be a compound of formula (III), wherein $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or is absent (e.g., $R^{12}$ is —$C_2$-alkyl-$CO_2^-$); $R^2$ is —$C_{17}H_{35}$, —$C_{17}H_{33}$, or —$C_{17}H_{31}$; $R^4$ is hydrogen; and $R^5$ is hydrogen.

It is to be understood, whether explicitly set forth or not, that formula (I), formula (II), and formula (III) are each intended to encompass the tautomeric, racemic, enantiomeric, diastereomeric, zwitterionic, and salt forms of said formulas. The imidazolines can exist in a zwitterionic form where $R^3$ and/or $R^x$ is derived from an acrylic acid.

The imidazoline compound can be present in the compositions in an amount of 1 wt % to 50 wt %, 2 wt % to 40 wt %, 3 wt % to 30 wt %, 4 wt % to 20 wt %, 5 wt % to 17 wt %, 6 wt % to 16 wt %, 7 wt % to 15 wt %, 8 wt % to 14 wt %, 9 wt % to 13 wt %, or 10 wt % to 12 wt %, based on total weight of the composition. The imidazoline compound can constitute about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, or about 20 wt % of the composition, based on total weight of the composition. The composition can comprise about 11 wt % of the imidazoline compound, based on total weight of the composition. The composition can comprise 11 wt % of the imidazoline compound, based on total weight of the composition.

b. Quaternary Amines

The compositions disclosed herein include a quaternary amine. Suitable quaternary amines include, but are not limited to, alkyl, hydroxyalkyl, alkylaryl, arylalkyl or arylamine quaternary salts.

Suitable alkyl, hydroxyalkyl, alkylaryl arylalkyl or arylamine quaternary salts include those alkylaryl, arylalkyl and arylamine quaternary salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I. For the quaternary amine, $R^{5a}$, $R^{6a}$, $R^{7a}$, and $R^{8a}$ can each independently be selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I.

Suitable quaternary ammonium salts include, but are not limited to, tetramethyl ammonium chloride, tetraethyl ammonium chloride, tetrapropyl ammonium chloride, tetrabutyl ammonium chloride, tetrahexyl ammonium chloride, tetraoctyl ammonium chloride, benzyltrimethyl ammonium chloride, benzyltriethyl ammonium chloride, phenyltrimethyl ammonium chloride, phenyltriethyl ammonium chloride, cetyl benzyldimethyl ammonium chloride, hexadecyl trimethyl ammonium chloride, dimethyl alkyl benzyl quaternary ammonium compounds, monomethyl dialkyl benzyl quaternary ammonium compounds, trimethyl benzyl quaternary ammonium compounds, and trialkyl benzyl quaternary ammonium compounds, wherein the alkyl group can contain between about 1 and about 24 carbon atoms, about 10 and about 18 carbon atoms, or about 12 to about 16 carbon atoms, such as for example, $C_{12-16}$ benzyl dimethyl ammonium chloride. Suitable quaternary ammonium compounds (quats) include, but are not limited to, trialkyl, dialkyl, dialkoxy alkyl, monoalkoxy, benzyl, and imidazolinium quaternary ammonium compounds, salts thereof, the like, and combinations thereof. The quaternary ammonium salt can be an alkylamine benzyl quaternary ammonium salt, a benzyl triethanolamine quaternary ammonium salt, or a benzyl dimethylaminoethanolamine quaternary ammonium salt.

The quaternary amine can be a benzalkonium salt represented by the formula:

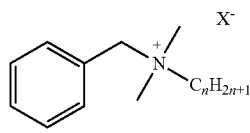

wherein n is 8, 10, 12, 14, 16, or 18; and X is Cl, Br or I.

The quaternary amine can be a mixture of benzalkonium salts wherein n is 8, 10, 12, 14, 16, and 18.

The quaternary amine can be a mixture of benzalkonium salts wherein n is 12, 14, 16, and 18.

The quaternary amine can be a mixture of benzalkonium salts wherein n is 12, 14, and 16.

The quaternary amine can be a mixture of benzalkonium salts wherein n is 12, 14, 16, and 18 and X is Cl.

The quaternary amine can be a mixture of benzalkonium salts wherein n is 12, 14, and 16, and X is Cl.

The quaternary amine can be an alkyl pyridinium quaternary salt such as those represented by the general formula:

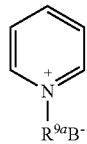

wherein $R^{9a}$ is an alkyl group, an aryl group, or an arylalkyl group, wherein said alkyl groups have from 1 to about 18 carbon atoms and B is Cl, Br or I. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium and an alkyl benzyl pyridinium chloride, preferably wherein the alkyl is a $C_1$-$C_6$ hydrocarbyl group.

The quaternary amine can be present in the compositions in an amount of 0.1 wt % to 80 wt %, 1 wt % to 40 wt %, 5 wt % to 35 wt %, 10 wt % to 30 wt %, 15 wt % to 25 wt %, 16 wt % to 24 wt %, 17 wt % to 23 wt %, 18 wt % to 22 wt %, or 19 wt % to 21 wt %, based on total weight of the composition. The quaternary amine constitutes about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, or about 35 wt % of the composition, based on total weight of the composition. The quaternary amine is present in an amount of about 20 wt % or about 21 wt %, based on total weight of the composition. The quaternary amine is present in an amount of 20.5 wt %, based on total weight of the composition.

The composition can include 5 wt % to 35 wt % of quaternary amine comprising $C_{12}$-benzyl dimethyl ammonium chloride (e.g., 4 wt % to 20 wt %, based on total weight of the composition), $C_{14}$-benzyl dimethyl ammonium chloride (e.g., 1 wt % to 10 wt %, based on total weight of the composition), $C_{16}$-benzyl dimethyl ammonium chloride (e.g., 0.1 wt % to 5 wt %, based on total weight of the composition), and $C_{18}$-benzyl dimethyl ammonium chloride (e.g., 0.5 wt % or less, based on total weight of the composition). The composition can include about 20 wt % or about 21 wt % of quaternary amine comprising $C_{12}$-benzyl dimethyl ammonium chloride (e.g., 14.5 wt %, based on total weight of the composition), $C_{14}$-benzyl dimethyl ammonium chloride (e.g., 5 wt %, based on total weight of the composition), $C_{16}$-benzyl dimethyl ammonium chloride (e.g., 1 wt %, based on total weight of the composition), and $C_{18}$-benzyl dimethyl ammonium chloride (e.g., 0.2 wt % or less, based on total weight of the composition).

c. Phosphonium Compounds

The compositions disclosed herein include at least one phosphonium compound, and in particular, a phosphonium salt. Suitable phosphonium salts include, but are not limited to, alkyltris(hydroxyorgano)phosphonium salts, alkenyltris(hydroxyorgano)phosphonium salts, and tetrakis(hydroxyorgano)phosphonium salts. The alkyltris(hydroxyorgano)phosphonium salts can be $C_1$-$C_3$-alkyltris(hydroxymethyl) phosphonium salts. The alkenyltris(hydroxyorgano) phosphonium salts can be $C_2$-$C_3$-alkenyltris(hydroxymethyl) phosphonium salts. The tetrakis(hydroxyorgano) phosphonium salts can be tetrakis(hydroxymethyl) phosphonium salts, including, but not limited to, tetrakis(hydroxymethyl)phosphonium sulphate (THPS), tetrakis(hydroxymethyl)phosphonium chloride, tetrakis(hydroxymethyl)phosphonium phosphate, tetrakis(hydroxymethyl)phosphonium formate, tetrakis(hydroxymethyl)phosphonium acetate, and tetrakis(hydroxymethyl)phosphonium oxalate. The phosphonium salt can be tetrakis(hydroxymethyl)phosphonium sulphate (THPS).

The phosphonium salt can be present in the compositions in an amount of 0.1 wt % to 80 wt %, 0.5 wt % to 50 wt %, 1 wt % to 14 wt %, 2 wt % to 13 wt %, 3 wt % to 12 wt %, 4 wt % to 11 wt %, 5 wt % to 10 wt %, 6 wt % to 9 wt %, or 7 wt % to 8 wt %, based on total weight of the composition. The phosphonium salt constitutes about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, or about 14 wt % of the composition, based on total weight of the composition. The phosphonium salt can be present in an amount of about 7 wt %, based on total weight of the composition. The phosphonium salt can be present in an amount of 7.5 wt %, based on total weight of the composition.

d. Demulsifiers

The compositions disclosed herein can include a demulsifier (also referred to as an emulsion breaker). Suitable emulsion breakers include, but are not limited to, dodecylbenzylsulfonic acid (DDBSA), the sodium salt of xylenesulfonic acid (NAXSA), epoxylated and propoxylated compounds, anionic cationic and nonionic surfactants, and resins, such as polyoxyalkylenes, vinyl polymers, polyamines, polyamides, phenolics, and silicone polyethers. The emulsion breaker can be a vinyl polymer, such as: acrylic acid, polymer with t-butylphenol, formaldehyde, maleic anhydride, propylene oxide, and ethylene oxide (CAS Registry Number: 178603-70-8).

The demulsifier can be present in an amount of 0.1 wt % to 30 wt %, 0.5 wt % to 10 wt %, or 1 wt % to 5 wt %, based on total weight of the composition. The demulsifier constitutes about 1 wt %, about 2 wt %, about 3 wt %, about 4 wt %, or about 5 wt % of the composition, based on total weight of the composition. The compositions comprise about 2 wt % or about 3 wt % of the demulsifier, based on total weight of the composition. The composition comprises 2.6 wt % of the demulsifier, based on total weight of the composition.

e. Synergist

The compositions disclosed herein can include a synergistic component. Suitable synergist compounds include, but are not limited to, thioglycolic acid, 3,3'-dithiodipropionic acid, thiosulfate, thiourea, 2-mercaptoethanol, L-cysteine, and tert-butyl mercaptan. The synergistic compound can be 2-mercaptoethanol.

The synergist can be present in an amount of 0.01 wt % to 10 wt %, 0.1 wt % to 8 wt %, 0.5 wt % to 7 wt %, 1 wt % to 6 wt %, 2 wt % to 5 wt %, or 3 wt % to 4 wt %, based on total weight of the composition. The synergist can constitute about 0.5 wt %, about 1 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, or about 6.0 wt % of the composition, based on total weight of the composition. The composition can comprise about 3.5 wt % of the synergist, based on total weight of the composition. The composition can comprise 3.5 wt % of the synergist, based on total weight of the composition.

f. Solvents

The compositions disclosed herein can include a solvent. Suitable solvents include, but are not limited to, alcohols, hydrocarbons, ketones, ethers, aromatics, amides, nitriles, sulfoxides, esters, glycol ethers, aqueous systems, and combinations thereof. The solvent can be water, isopropanol, methanol, ethanol, 2-ethylhexanol, heavy aromatic naphtha, toluene, ethylene glycol, ethylene glycol monobutyl ether (EGMBE), diethylene glycol monoethyl ether, or xylene. Representative polar solvents suitable for formulation with the composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like. Representative non-polar solvents suitable for formulation with the composition include aliphatics such as pentane, hexane, cyclohexane, methylcyclohexane, heptane, decane, dodecane, diesel, and the like; aromatics such as toluene, xylene, heavy aromatic naphtha, fatty acid derivatives (acids, esters, amides), and the like.

The solvent can be methanol, isopropanol, 2-ethylhexanol, or a combination thereof. Further, the solvent can be methanol, isopropanol, 2-ethylhexanol, water, or a combination thereof.

A composition of the invention can comprise from 0 to 99 percent, 1 to 98 percent, 10 to 80 percent, 20 to 70 percent, 30 to 60 percent, or 40 to 55 percent by weight of one or more solvents, based on total weight of the composition.

A composition of the invention can comprise about 20%, about 25%, about 30%, about 35%, about 40%, about 45%, about 50%, about 55%, about 60%, about 65%, about 70%, about 75%, about 80%, about 85%, about 90%, or about 95% by weight of one or more solvents, based on total weight of the composition. A composition of the invention comprises about 40% of one or more alcoholic solvents and about 15% of water. A composition of the invention can comprise about 40% of a methanol/isopropanol mixture and about 15% of water. A composition of the invention can comprise 40% of a methanol/isopropanol mixture and 14.9% of water.

The compositions of the invention optionally include one or more additional additives. Suitable additives include, but are not limited to, corrosion inhibitors, asphaltene inhibitors, paraffin inhibitors, scale inhibitors, emulsifiers, water clarifiers, dispersants, hydrogen sulfide scavengers, gas hydrate inhibitors, biocides, pH modifiers, and surfactants.

g. Corrosion Inhibitors

Suitable corrosion inhibitors for inclusion in the compositions include, but are not limited to, mono-, di- or trialkyl or alkylaryl phosphate esters; phosphate esters of hydroxylamines; phosphate esters of polyols; and monomeric or oligomeric fatty acids.

Suitable mono-, di- and trialkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethyl phosphate with triethylphosphate producing a more broad distribution of alkyl phosphate esters. Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor can be a monomeric or oligomeric fatty acid. Preferred are $C_{14}$-$C_{22}$ saturated and unsaturated fatty acids as well as dimer, trimer and oligomer products obtained by polymerizing one or more of such fatty acids.

h. Asphaltene Inhibitors

Suitable asphaltene inhibitors include, but are not limited to, aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

i. Paraffin Inhibitors

Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable dispersants include, but are not limited to, dodecyl benzene sulfonate, oxyalkylated alkylphenols, and oxyalkylated alkylpnenolic resins.

j. Scale Inhibitors

Suitable scale inhibitors include, but are not limited to, phosphates, phosphate esters, phosphoric acids, phosphonates, phosphonic acids, polyacrylamides, salts of acrylamido-methyl propane sulfonate/acrylic acid copolymer (AMPS/AA), phosphinated maleic copolymer (PHOS/MA), and salts of a polymaleic acid/acrylic acid/acrylamido-methyl propane sulfonate terpolymer (PMA/AMPS).

k. Emulsifiers

Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

l. Water Clarifiers

Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DAD-MAC).

m. Dispersants

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate) and the triamine- and tetramine-polymethylene phosphonates with 2-4 methylene groups between each N atom, at least 2 of the numbers of methylene groups in each phosphonate being different. Other suitable dispersion agents include lignin or derivatives of lignin such as lignosulfonate and naphthalene sulfonic acid and derivatives.

n. Hydrogen Sulfide Scavengers

Suitable additional hydrogen sulfide scavengers include, but are not limited to, oxidants (e.g., inorganic peroxides such as sodium peroxide, or chlorine dioxide), aldehydes (e.g., of 1-10 carbons such as formaldehyde or glutaraldehyde or (meth)acrolein), triazines (e.g., monoethanol amine triazine, monomethylamine triazine, and triazines from multiple amines or mixtures thereof), and glyoxal.

o. Gas Hydrate Inhibitors

Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, NaCl salt, KCl salt, $CaCl_2$ salt, $MgCl_2$ salt, $NaBr_2$ salt, formate brines (e.g. potassium formate), polyols (such as glucose, sucrose, fructose, maltose, lactose, gluconate, monoethylene glycol, diethylene glycol, triethylene glycol, monopropylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate). Suitable kinetic hydrate inhibitors and anti-agglomerates include, but are not limited to, polymers and copolymers, polysaccharides (such as hydroxy-ethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

p. Biocides

Suitable additional biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., bronopol and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

q. pH Modifiers

Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include NaOH, KOH, $Ca(OH)_2$, CaO, $Na_2CO_3$, $KHCO_3$, $K_2CO_3$, $NaHCO_3$, MgO, and $Mg(OH)_2$.

r. Surfactants

Suitable surfactants include, but are not limited to, anionic surfactants, cationic surfactants, zwitterionic surfactants, and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Cationic surfactants include alkyl trimethyl quaternary ammonium salts, alkyl dimethyl benzyl quaternary ammonium salts, dialkyl dimethyl quaternary ammonium salts, and imidazolinium salts. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodiproprionate.

The surfactant can be a quaternary ammonium compound, an amine oxide, an ionic or non-ionic surfactant, or any combination thereof. Suitable quaternary amine compounds include, but are not limited to, alkyl benzyl ammonium chloride, benzyl cocoalkyl($C_{12}$-$C_{18}$)dimethylammonium chloride, dicocoalkyl ($C_{12}$-$C_{18}$)dimethylammonium chloride, ditallow dimethylammonium chloride, di(hydrogenated tallow alkyl)dimethyl quaternary ammonium methyl chloride, methyl bis(2-hydroxyethyl cocoalkyl($C_{12}$-$C_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, and hydrogenated tallow alkyl (2-ethylhyexyl) dimethyl quaternary ammonium methyl sulfate.

s. Additional Components

Compositions made according to the invention can further include additional functional agents or additives that provide a beneficial property. Additional agents or additives will vary according to the particular composition being manufactured and its intended use as one skilled in the art will appreciate.

Alternatively, the compositions do not contain any of the additional agents or additives.

3. Synthesis

The compounds and compositions of the invention can be better understood in connection with the following synthetic schemes and methods which illustrate a means by which the compounds can be prepared.

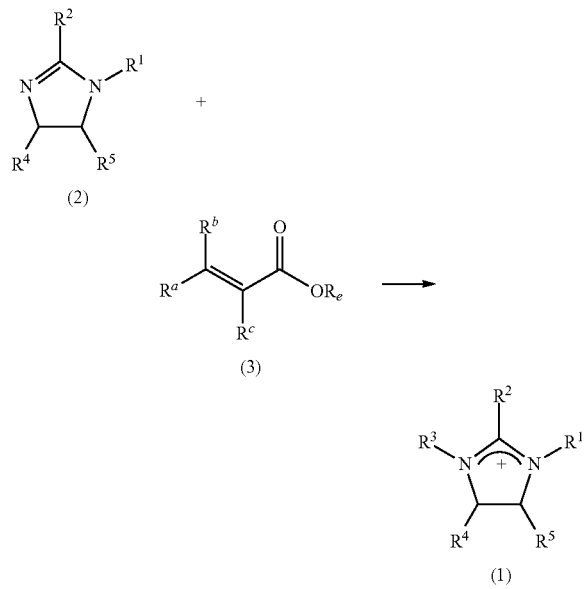

As shown in Scheme 1, compounds of formula (1) can be prepared by reacting an imidazoline of formula (2) with an acrylic acid of formula (3), wherein $R^1$, $R^2$, $R^3$, $R^4$, $R^5$, $R^a$, $R^b$, $R^c$, and $R^e$ are as defined above. The imidazoline of formula (2) can be prepared from reacting a diamine, such as ethylene diamine (EDA), diethylene triamine (DETA), or triethylene tetraamine (TETA) with a long chain fatty acid, such as tall oil fatty acid (TOFA). The compound of formula (3) introduced in the representative reaction schemes generally include α,β-unsaturated carboxylic fatty acids and amide and ester derivatives thereof; unsaturated sulfonic and phosphonic fatty acids; and their combinations. The compound of formula (3) can be selected from the group consisting of substituted and unsubstituted α,β-unsaturated carboxylic fatty acids and amide and ester derivatives thereof, having from 3 to about 11 carbon atoms, or a salt thereof; substituted and unsubstituted α,β-unsaturated fatty acids having from 2 to about 11 carbon atoms, or a salt thereof; and combinations thereof For Scheme 1, $R^4$, $R^5$, $R^a$, $R^b$, $R^c$, and $R^e$ are each hydrogen. Additionally, $R^1$ is $C_2$-$C_{10}$-alkyl, $C_2$-$C_8$-alkyl, or $C_2$-$C_6$-alkyl; and $R^4$, $R^5$, $R^a$, $R^b$, $R^c$, and $R^e$ are each hydrogen. Further, $R^1$ is $C_2$-$C_{10}$-alkyl, $C_2$-$C_8$-alkyl, or $C_2$-$C_6$-alkyl; $R^2$ is a $C_{17}$ radical; and $R^4$, $R^5$, $R^a$, $R^b$, $R^c$, and $R^e$ are each hydrogen. Also, $R^1$ is $C_2$-$C_{10}$-alkyl, $C_2$-$C_8$-alkyl, or $C_2$-$C_6$-alkyl; $R^2$ is a radical derived from coconut oil, beef tallow, or tall oil fatty acids (TOFA); and $R^4$, $R^5$, $R^a$, $R^b$, $R^c$, and $R^e$ are each hydrogen.

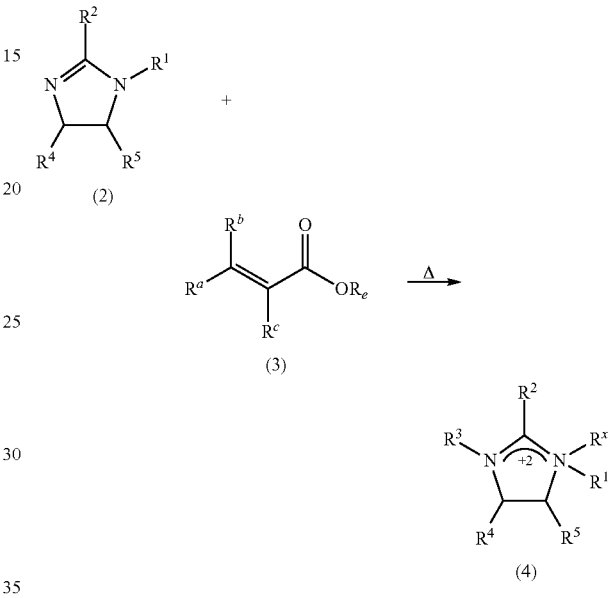

As shown in Scheme 2, compounds of formula (4) can be prepared by reacting an imidazoline of formula (2) with an acrylic acid of formula (3), wherein $R^1$, $R^2$, $R^3$, $R^x$, $R^4$, $R^5$, $R^a$, $R^b$, $R^c$, and $R^e$ are as defined above.

For Scheme 2, $R^4$, $R^5$, $R^a$, $R^b$, $R^c$, and $R^e$ are each hydrogen. Additionally, $R^1$ is linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_{17}H_{33}$, or —$C_{17}H_{31}$; $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen (—H), $C_1$-$C_6$-alkyl, or $R^e$ is absent (e.g., $R^3$ is —$CH_2CH_2CO_2^-$); $R^x$ is —$CH_2CH_2CO_2R^e$, wherein $R^e$ is hydrogen (—H), $C_1$-$C_6$-alkyl, or $R^e$ is absent (e.g., $R^x$ is —$CH_2CH_2CO_2^-$); $R^4$ is hydrogen; and $R^5$ is hydrogen. Further, $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or is absent (e.g., $R^{12}$ is —$C_2$-alkyl-$CO_2^-$); $R^2$ is —$C_{17}H_{35}$, —$C_{17}H_{33}$, or —$C_{17}H_{31}$; $R^3$ is —$CH_2CH_2CO_2R^e$, wherein $R^e$ is hydrogen (—H), $C_1$-$C_6$-alkyl, or $R^e$ is absent (e.g., $R^3$ is —$CH_2CH_2CO_2^-$); $R^x$ is —$CH_2CH_2CO_2R^e$, wherein $R^e$ is hydrogen (—H), $C_1$-$C_6$-alkyl, or $R^e$ is absent (e.g., $R^x$ is —$CH_2CH_2CO_2^-$); $R^4$ is hydrogen; and $R^5$ is hydrogen.

Imidazolines for use with compositions of the invention can also be commercially available.

The compounds can be further modified, for example, by manipulation of substituents. These manipulations can include, but are not limited to, reduction, oxidation, organometallic cross-coupling, alkylation, acylation, and hydrolysis reactions which are commonly known to those skilled in the art. In some cases, the order of carrying out the foregoing reaction schemes can be varied to facilitate the reaction or to avoid unwanted reaction products.

4. Methods of Use

The compositions of the invention can be used in any industry where it is desirable to control biofouling and/or inhibit corrosion at a surface. The compositions can preferably be used as biocides for use in oil and gas applications. By treating a gas or liquid stream with an effective amount of a composition of the invention, the compositions can provide significant planktonic kill and enhanced biofilm control by delaying regrowth kinetics of the biofilms.

The compositions can be used in water systems, condensate/oil systems/gas systems, or any combination thereof.

The compositions can be applied to a gas or liquid produced or used in the production, transportation, storage, and/or separation of crude oil or natural gas.

The compositions can be applied to a gas stream used or produced in a coal-fired process, such as a coal-fired power plant.

The compositions can be applied to a gas or liquid produced or used in a waste-water process, a farm, a slaughter house, a land-fill, a municipality waste-water plant, a coking coal process, or a biofuel process.

A fluid to which the compositions can be introduced can be an aqueous medium. The aqueous medium can comprise water, gas, and optionally liquid hydrocarbon. A fluid to which the compositions can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid or gas can be a refined hydrocarbon product.

A fluid or gas treated with a composition of the invention can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C.

The compositions of the invention can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the compositions of the invention are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units. The fluid or gas can be contained in water systems, condensate/oil systems/gas systems, or any combination thereof.

The compositions of the invention can be introduced into a fluid or gas by any appropriate method for ensuring dispersal through the fluid or gas. The inhibitor composition is added at a point in a flow line upstream from the point at which corrosion prevention is desired. The compositions can be injected using mechanical equipment such as chemical injection pumps, piping tees, injection fittings, atomizers, quills, and the like. The compositions of the invention can be introduced with or without one or more additional polar or non-polar solvents depending upon the application and requirements. The compositions of the invention can be pumped into an oil and/or gas pipeline using an umbilical line. Capillary injection systems can be used to deliver the compositions to a selected fluid. The compositions can be introduced into a liquid and mixed. The compositions can be injected into a gas stream as an aqueous or nonaqueous solution, mixture, or slurry. The fluid or gas can be passed through an absorption tower comprising a compound or composition of the invention.

The compositions can be applied to a fluid or gas to provide any selected concentration. In practice, the compositions of the invention are typically added to a flow line to provide an effective treating dose of the described compositions from about 0.01 to about 10,000 ppm. The compositions can be applied to a fluid or gas to provide a total actives (e.g., imidazoline, quaternary amine, phosphonium salt, demulsifier, and synergist) concentration of about 1 parts per million (ppm) to about 1,000,000 ppm, about 1 ppm to about 100,000 ppm, about 10 ppm to about 75,000 ppm, about 10 ppm to about 10,000 ppm, about 50 ppm to about 10,000 ppm, or about 100 ppm to about 500 ppm. The compositions can be applied to a fluid to provide an actives concentration of about 10 ppm to about 10,000 ppm, about 10 ppm to about 500 ppm, about 50 ppm to about 500 ppm, or about 100 ppm to about 500 ppm. The compositions are applied to a fluid or gas to provide an actives concentration of about 50 ppm, about 100 ppm, about 150 ppm, about 200 ppm, about 250 ppm, about 300 ppm, about 350 ppm, about 400 ppm, about 450 ppm, about 500 ppm, about 550 ppm, about 600 ppm, about 650 ppm, about 700 ppm, about 750 ppm, about 800 ppm, about 850 ppm, about 900 ppm, about 950 ppm, or about 1,000 ppm. Each system can have its own dose level requirements, and the effective dose level of a composition to sufficiently reduce the rate of corrosion can vary with the system in which it is used.

The compositions can be applied continuously, in batch, or a combination thereof. The composition doses can be continuous.

The composition doses can be intermittent (i.e., batch treatment).

The composition doses can be continuous/maintained and/or intermittent.

Dosage rates for continuous treatments typically range from about 10 to about 500 ppm, or about 10 to about 200 ppm.

Dosage rates for batch treatments typically range from about 10 to about 10,000 ppm.

The composition can be applied as a pill to a pipeline, providing a high dose (e.g., 10,000 ppm) of the composition.

The flow rate of a flow line in which the composition is used can be between 0 and 100 feet per second, or between 0.1 and 50 feet per second. In some cases, the compositions can be formulated with water in order to facilitate addition to the flow line.

The compositions can provide 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% planktonic kill. The compositions can provide 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% planktonic kill in a dynamic flow loop test after a 4-hour contact period with the biocide composition.

The dynamic flow loop can be characterized by a test system that holds approximately a selected volume of fluid (e.g., 1.5 liters) that are continually circulated over 1018 carbon steel biostuds (e.g., located in the 6 o'clock position of a modified Robbin's device). The test fluid can be pumped through the system at a selected rate (e.g., approximately 3.1 gallons per minute), which allows for deposition of microorganisms and solids onto the biostuds. The health of the microbial population can be monitored (e.g., weekly) during the biofilm growth period (e.g., 7 weeks) using ATP quantification. After concluding the establishment of a mature biofilm, a biocide efficacy study can be initiated. During the study, solid and fluid samples can be collected before and after the biocide treatment at scheduled intervals (e.g., 4 hours, 24 hours, 72 hours, or 120 hours). A baseline reading (e.g., solid and fluid samples) can be taken prior to the addition of the biocide to the individual flow loop. To study how quickly a biofilm is able to regrow after batch biocide treatment, the total biocide-treated fluid in each flow loop can be removed from the system and untreated production fluid added back into the system. Additional solid samples (e.g., biostuds) can be removed at selected time intervals (e.g., 24, 48 and either 72 or 120-hours) after the new fluid was added, so as to determine how quickly the biofilm was able to regrow to its pretreatment size.

The compounds, compositions, methods, and processes of the invention will be better understood by reference to the following examples, which are intended as an illustration of and not a limitation upon the scope of the invention.

5. Examples

The foregoing can be better understood by reference to the following examples, which are presented for purposes of illustration and are not intended to limit the scope of the invention.

Imidazolines can be prepared as described in Examples 1-5, and as described in U.S. Pat. Nos. 6,488,868, 7,057,050, and 7,951,754, the contents of which are hereby incorporated by reference in their entirety. Imidazolines can also be commercially available.

Example 1

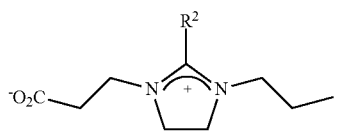

To prepare the imidazoline above wherein $R^2$ is $-C_{17}H_{35}$, $-C_{17}H_{33}$, or $-C_{17}H_{31}$, sixty grams of Tall Oil Fatty Acid (TOFA) was placed in a 250 ml, 4-neck flask equipped with an overhead stirrer, thermocouple, addition funnel and a Dean-Stark trap. The TOFA was heated to 60° C. and then 25 grams of N-propyl-ethylenediamine was added dropwise rapidly. The resulting mixture turned from light yellow to dark red and exothermed to 100° C. The mixture was then heated to 120-140° C. for 3 hours. The hydrocarbon collected in the trap was returned to the flask. The mixture was thereafter heated to 160° C. for 1 hour while allowing water to collect in the Dean-Stark trap.

The resulting mixture was then heated at 165° C. for 2 hours and then at 225° C. for an additional hour during which time any further evolved water was collected. A nitrogen sweep was applied and the speed of the overhead stirrer was increased to facilitate removal of water. Following further heating of the mixture to 225° C. for an additional 1.5 hours, the reaction mixture was cooled and 65.9 grams of the resulting imidazoline mixture was then reacted with 18.7 grams of acrylic acid which was carefully added dropwise to the imidazoline product. A temperature rise of about 70-89° C. was observed. After exotherm had ceased, the reaction temperature was raised to about 100° C. for 2 hours. The resulting N-propyl-2-heptadecenyl imidazoline acrylate was recovered.

Example 2

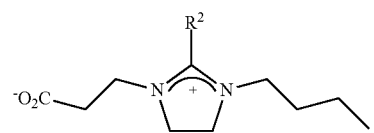

To prepare the imidazoline above wherein R is $-C_{17}H_{35}$, $-C_{17}H_{33}$ or $-C_{17}H_{31}$, sixty grams of Tall Oil Fatty Acid (TOFA) was placed in a 250 ml, 4-neck flask equipped with an overhead stirrer, thermocouple, addition funnel and a Dean-Stark trap. The TOFA was heated to 60° C. and then 28.5 grams (0.245 mol) of N-butylethylenediamine was added dropwise rapidly. The resulting mixture turned from light yellow to dark red and exothermed to 84° C. The mixture was then heated to 160° C. for 3.5 hours until no further water evolved. The hydrocarbon collected in the trap was returned to the flask. The mixture was thereafter heated to 160° C. for 1 hour while allowing water to collect in the Dean-Stark trap.

Fifty grams (0.132 mole) of the resulting mixture was then heated at 225° C. for an additional hour during which time any further evolved water was collected. A nitrogen sweep was applied and the speed of the overhead stirrer was increased to facilitate removal of water. Following further heating of the mixture to 225° C. for an additional 1.5 hours, the reaction mixture was cooled and 45.25 grams of the resulting imidazoline mixture was then reacted with 10.4 grams of acrylic acid which was carefully added dropwise to the imidazoline product. A temperature rise to about 88° C. was observed. After exotherm had ceased, the reaction temperature was raised to about 120° C. for 2 hours. The resulting N-butyl-2-heptadecenyl imidazoline acrylate was recovered.

Example 3

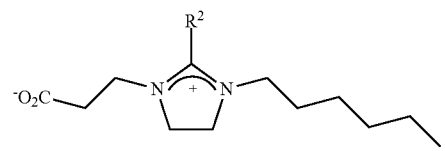

To prepare the imidazoline above wherein $R^2$ is —$C_{17}H_{35}$, —$C_{17}H_{33}$ or —$C_{17}H_{31}$, sixty grams of Tall Oil Fatty Acid (TOFA) was placed in a 250 ml, 4-neck flask equipped with an overhead stirrer, thermocouple, addition funnel and a Dean-Stark trap. The TOFA was heated to 60° C. and 35.3 grams (0.265 mol) of N-hexylethylenediamine was added dropwise rapidly. The resulting mixture turned from light yellow to dark red and exothermed to 87° C. The mixture was heated to 160° C. for 3.5 hours until no further water evolved. The hydrocarbon collected in the trap was returned to the flask. The mixture was thereafter heated at 160° C. for 1 hour while allowing water to collect in the Dean-Stark trap.

Sixty one grams of the resulting mixture was then heated at 225-230° C. for an hour and then at 225° C. for an additional hour during which time any further evolved water was collected. A nitrogen sweep was applied and the speed of the overhead stirrer was increased to facilitate removal of water. Following further heating of the mixture to 225° C. for an additional 1.5 hours, the reaction mixture was cooled and 55.93 grams of the resulting imidazoline mixture was then reacted in a 3-neck 250 ml flask with 18.7 grams of acrylic acid which was carefully added dropwise to the imidazoline product. A temperature rise to about 92° C. was observed. After exotherm had ceased, the reaction temperature was raised to about 120° C. for 2 hours. The resulting N-hexyl-2-heptadecenyl imidazoline acrylate was recovered.

Example 4

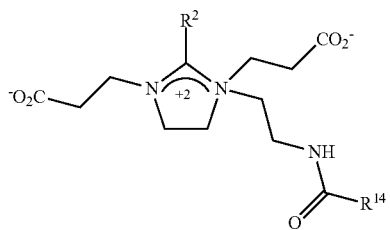

To prepare the imidazoline compound above wherein $R^2$ and $R^{14}$ are independently —$C_{17}H_{35}$, —$C_{17}H_{33}$ or —$C_{17}H_{31}$, 220.4 grams (0.78 moles) of a tall oil fatty acid mixture ("TOFA"-comprised of about 46% oleic acid, about 41% linoleic acid, about 4% stearic acid, and about 9% other acids) was weighed and placed into a 500 ml round bottom, four-neck flask equipped with an overhead stirrer, thermocouple, addition funnel, and Dean-Stark trap. The TOFA was heated to about 70° C. and 38.8 grams (0.38 moles) of diethylenetriamine was added dropwise, with stirring. An exotherm of about 35° C. was observed. The mixture was further heated at 130° C. for 1 hour and at 160° C. for 2 hours. The mixture was then held at 250° C. for 2 hours with a nitrogen gas sweep. 17.6 ml (about 86% theoretical amount of water for 100% imidazoline formation) of water was collected. The mixture was cooled and 60.8 grams (0.84 moles) of glacial acrylic acid was added dropwise, with stirring, which had an exotherm between 47 and 67° C. This final mixture was heated at 120 to 125° C. for 2 hours to ensure complete reaction.

Example 5

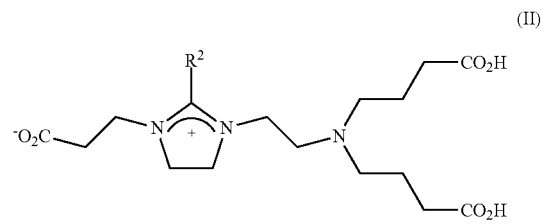

To prepare the imidazoline above wherein $R^2$ is —$C_{17}H_{35}$, —$C_{17}H_{33}$ or —$C_{17}H_{31}$, 175 g (0.62 mol) of TOFA was placed in a 500 mL round bottom four-neck flask equipped with an overhead stirrer, addition funnel, thermocouple and Dean-Stark trap. The acid was heated to 60° C. and a sweep of nitrogen gas was maintained over the surface of the liquid throughout the reaction. When the temperature reached 60° C., 82 g (0.8 mol) of DETA was added dropwise rapidly. An exotherm of about 40° C. was observed. The mixture was heated to 175° C. with stirring until the theoretical amount of water for amide formation (11 g) was collected. The infrared spectrum of the mixture at this point indicated the presence of amide (absorption at about 1630 and 1550 cm$^{-1}$) and free N—H (absorption at about 3315 cm$^{-1}$). The temperature was increased to 225° C. and maintained there for 2 hours (84% of the theoretical amount of water for 100% imidazoline formation was collected). The infrared spectrum exhibited the same two broad bands noted above and a sharper, intense band between them around 1610 cm$^{-1}$, indicative of imidazoline.

69.8 g (0.2 mol, presuming the composite molecular weight of the amine imidazoline is 349 g/mole) of the resultant amine imidazoline mixture was weighed into a 250 mL round bottom four-neck flask equipped with an overhead stirrer, addition funnel and thermocouple. To this was added 43.2 g (0.6 mol) acrylic acid via the addition funnel. The exotherm was noted and the mixture heated at 120° C. for 2 hours.

Biocide Testing

Evaluation of the biocide compositions disclosed herein was performed through a dynamic flow loop test where both planktonic and sessile organisms could be monitored. To start this testing, fluid from the field, as well as cultured organisms from the field, were placed into the system and allowed to grow for approximately 7 weeks, providing a mature biofilm that can then be challenged by the biocide treatment.

The test system holds approximately 1.5 liters of fluid that are continually circulated over 1018 carbon steel biostuds located in the 6 o'clock position of a modified Robbin's device. The device holds a maximum of eight biostuds in the 6 o'clock position. The production fluid was pumped through the system at a rate of approximately 3.1 gallons per minute, which allows for deposition of microorganisms and solids onto the biostuds. The health of the microbial population was monitored weekly during the biofilm growth period using ATP quantification.

After concluding the establishment of a mature biofilm, the sessile kill study was initiated. During the study, solid and fluid samples were collected before and after the biocide treatment at scheduled intervals. The following chemicals were tested in the system: (study 1) THPS was tested against THPS/quat #2, (study 2) THPS/quat #1, and (study 3) THPS/ quat/imidazoline. A baseline reading was taken, during all of the studies, prior to the addition of the chemical to the individual flow loop. This consisted of a fluid sample as well as two biostuds. After removal of the baseline sample, either (study 1) THPS or THPS/quat #2, (study 2) THPS/quat #1, (study 3) THPS/quat/imidazoline was added to a flow loop at the predetermine concentration with a 4 hour contact time. After the 4 hour treatment, a second fluid sample and two coupons were removed from each flow loop. The total fluid in each flow loop was then removed from the system and untreated production fluid added back to mimic a batch biocide treatment followed by continued production. Additional biostuds were removed at 24, 48 and either 72 or 120-hours after the new fluid was added to determine how quickly the biofilm was able to regrow to its pretreatment size.

One of the features of this chemistry is the enhanced biofilm kill that a formulation has when the imidazoline is present even though the imidazoline itself has no enhanced kill on planktonic organisms. FIG. 1 shows a planktonic biocide efficacy kill study where varying amounts of imidazoline were mixed with a biocidal quaternary. As the amount of the imidazoline was increased, the microbial kill decreased, as shows in FIG. 1.

Figure 2:
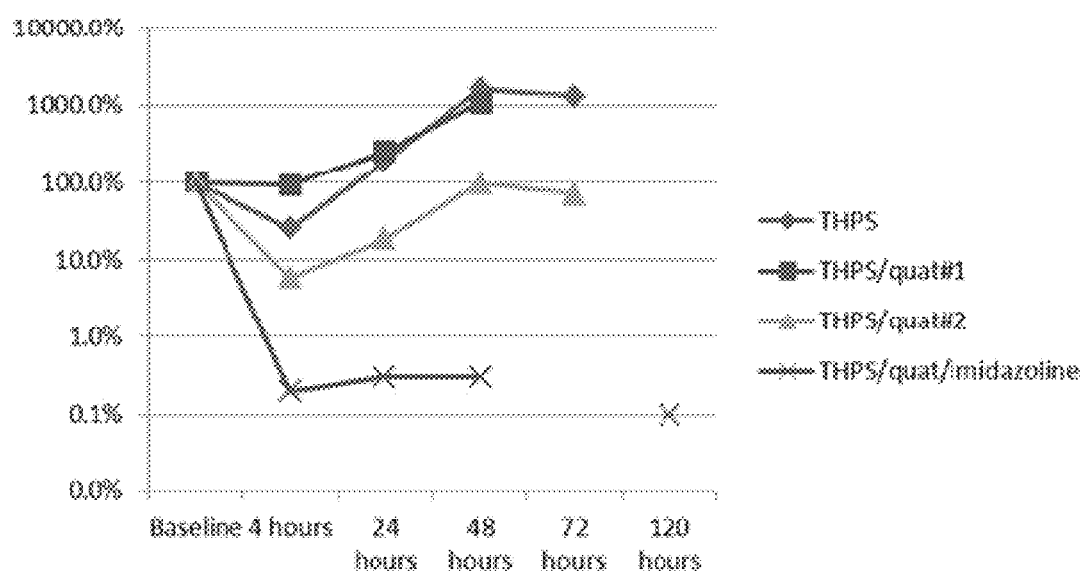
FIG. 2 depicts biocidal activity of compositions including one or more of an imidazoline, a quaternary amine, and a phosphonium salt.

FIG. 2 is a compilation of three separate experiments illustrating the ability to kill microbes present in a biofilm by using THPS alone, THPS in combination with one of two difcferent quats, or THPS with a quat plus the acrylated imidazoline. The initial data point before treatment is set to 100% and all other readings are reported as a percent change compared to the baseline. THPS alone provides initial biofilm kill, but the biofilm is larger than it was before treatment within 24 hours. THPS plus the quats provided enhanced control with quat #2 compared to THPS alone but no enhanced control with quat #1. Quat #2 was N,N-dimethyl, N-alkyl-benzylammonium chloride wherein the alkyl was a mixture of $C_{12}$, $C_{14}$, and $C_{16}$ alkyl groups. The imidazoline used was available commercially under the tradename Clean N Cor from Nalco. The THPS/quat/imidazoline provided a synergistic effect where biofilm growth was reduced to less than 0.3% of the initial size and maintained for at least 120 hours when the testing was stopped.

Planktonic kill in the dynamic flow loops was also evaluated immediately after a 4 hour contact time with the biocide. The results of that testing are shown in Table 1. Compared to THPS alone, the addition of a quat does provide some enhanced kill. The addition of a quat plus the imidazoline to THPS provided a synergistic effect where the planktonic kill was significantly enhanced compared to THPS or THPS plus quat only.

TABLE 1

Planktonic kill data

| Biocide | Dosage | % reduction |
|---|---|---|
| THPS | 112.5 ppm active THPS | 81.8% |
| THPS/quat #1 | 140 ppm active THPS | 94.4% |
| THPS/quat #2 | 52.5 ppm active THPS | 83.2% |
| THPS/quat #2 | 140 ppm active THPS | 91.0% |
| THPS/quat/imidazoline | 47.5 ppm active THPS | 99.8% | quat #1 = benzyl-($C_{12}$-$C_{16}$ linear alkyl)-dimethyl-ammonium chloride
quat #2 = same quat from the THPS/quat/imidazoline blend (without the imidazole)

Figure 3:
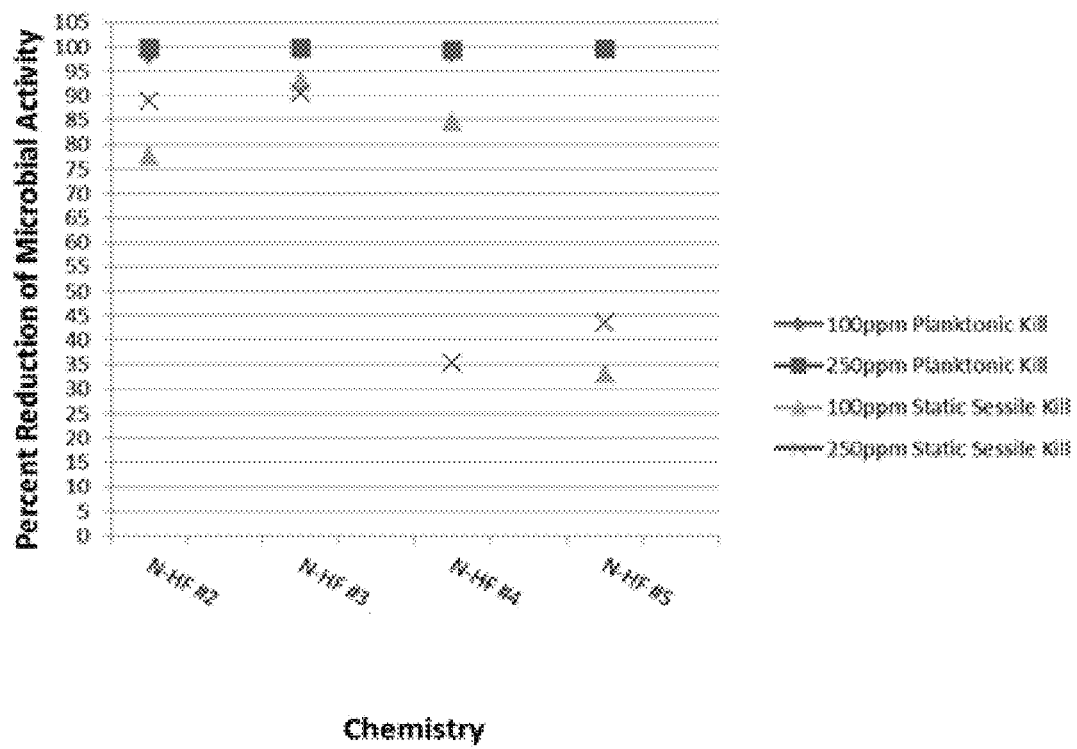
FIG. 3 depicts biocidal activity of compositions including varying ratios of imidazoline, quaternary amine, and phosphonium salt components.

Based on these results, a planktonic kill study, as described above, and a static sessile kill study were employed to determine the ratio of the THPS/quat/imidazoline that yields the most synergistic effect. The results indicated that the formulations titled N-HF #2 and N-HF #3 provided the best overall kill for both the planktonic and static sessile tests, as shown in FIG. 3. N-HF #2 contained 45 wt. % Clean N Cor and N-HF #3 contained 40 wt. % Clean N Cor.c Additional formulations were prepared with an emulsion breaker to enhance oil/water separation when using the synergistic biocide formulations. For this test, synthetic brine and crude from the field were added to a 250 mL flask. After the addition of the designated chemistry, the flask was mixed for 30 seconds at 2000 rpm. Once the mixing was completed, the height of each layer was recorded after 5, 20, and 60 minutes.

Figure 4:
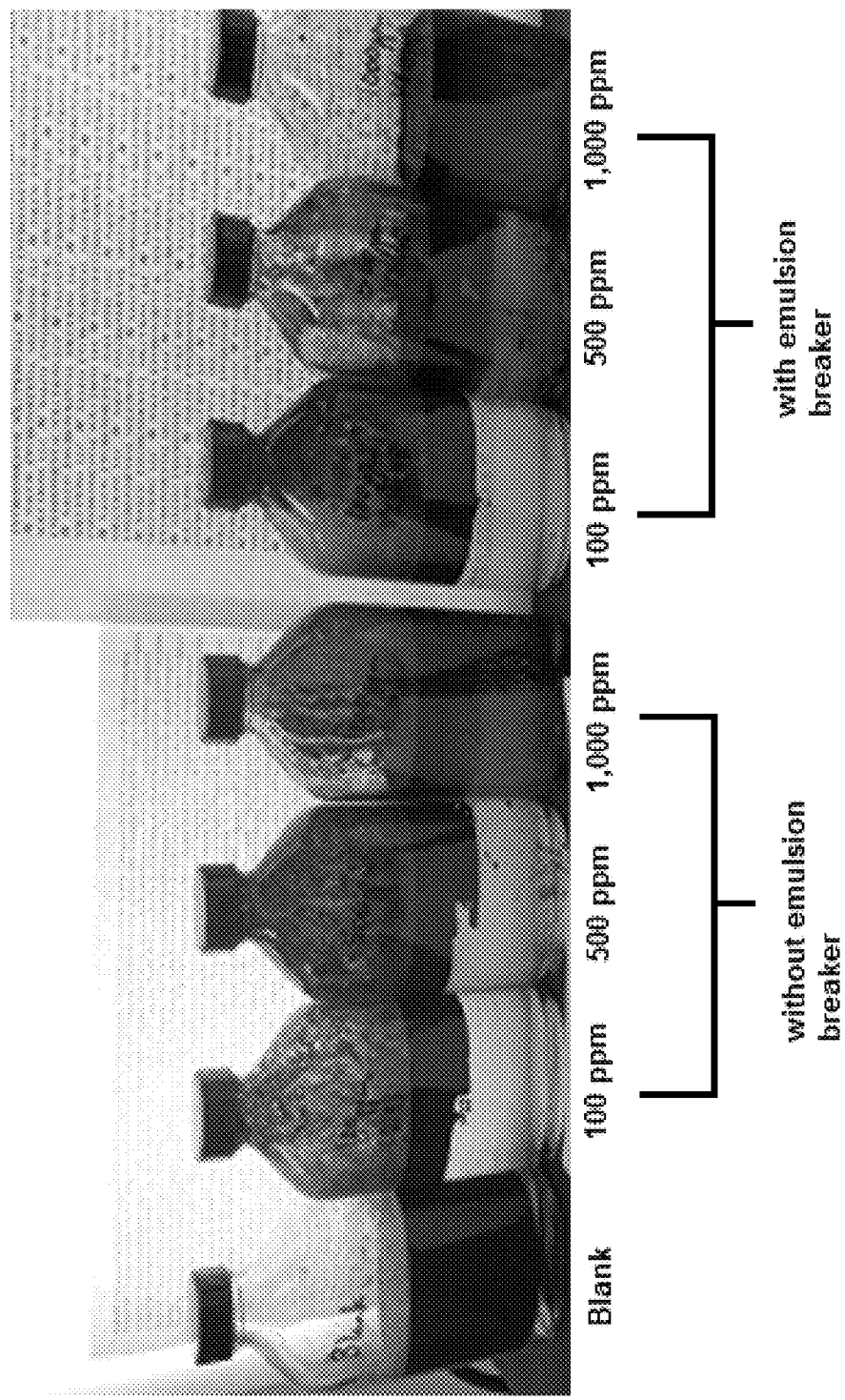
FIG. 4 depicts an emulsion tendency study.

FIG. 4 shows the blank, or negative control, against the synergistic biocide formulation without the emulsion breaker and the synergistic biocide formulation with the emulsion breaker at concentrations of 100 ppm, 500 ppm, and 1000 ppm, after 20 minutes. Observations revealed the crude emulsion seems to be tighter with the formulation including the emulsion breaker than formulation without the emulsion breaker. This provides an additional benefit to the biocide formulations.

After determining the ratio that yields the most synergistic effects and the addition of the emulsion breaker, an exemplary biocide formulation according to Table 2 was prepared. A sessile kill study was conducted to determine the efficacy of the formulation of Table 2. This test revealed a 98.6% reduction in the planktonic community and a 95.2% reduction in the sessile community after a 4 hour contact time.

TABLE 2

| Component | | (wt %) |
|---|---|---|
| Imidazoline | imidazoline(s) of formula (I): | 11 |

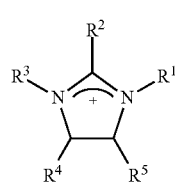

(I)

wherein $R^1$ is substituted alkyl; $R^2$ is —$C_{17}H_{35}$, —$C_{17}H_{33}$, or —$C_{17}H_{31}$; $R^3$ is —$CH_2CH_2CO_2^-$; $R^4$ is H; and $R^5$ is H TABLE 2-continued

| | Component | (wt %) |
|---|---|---|
| Quaternary Amine | benzalkonium salts of the formula:<br>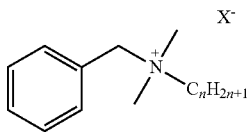<br>wherein n is 12, 14, 16, and/or 18; and X is Cl | 20.5 |
| Phosphonium Salt | tetrakis(hydroxymethyl)phosphonium sulphate (THPS):<br>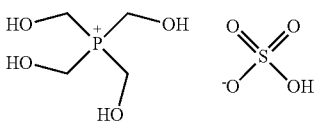 | 7.5 |
| Demulsifier | acrylic acid, polymer with t-butylphenol, formaldehyde, maleic anhydride, propylene oxide, and ethylene oxide (CAS Registry Number: 178603-70-8) | 2.6 |
| Synergist | 2-mercaptoethanol | 3.5 |
| Alcoholic Solvent | methanol/isopropanol | 40 |
| Aqueous Solvent | Water | 14.9 |

Example 6

Figure 5A:
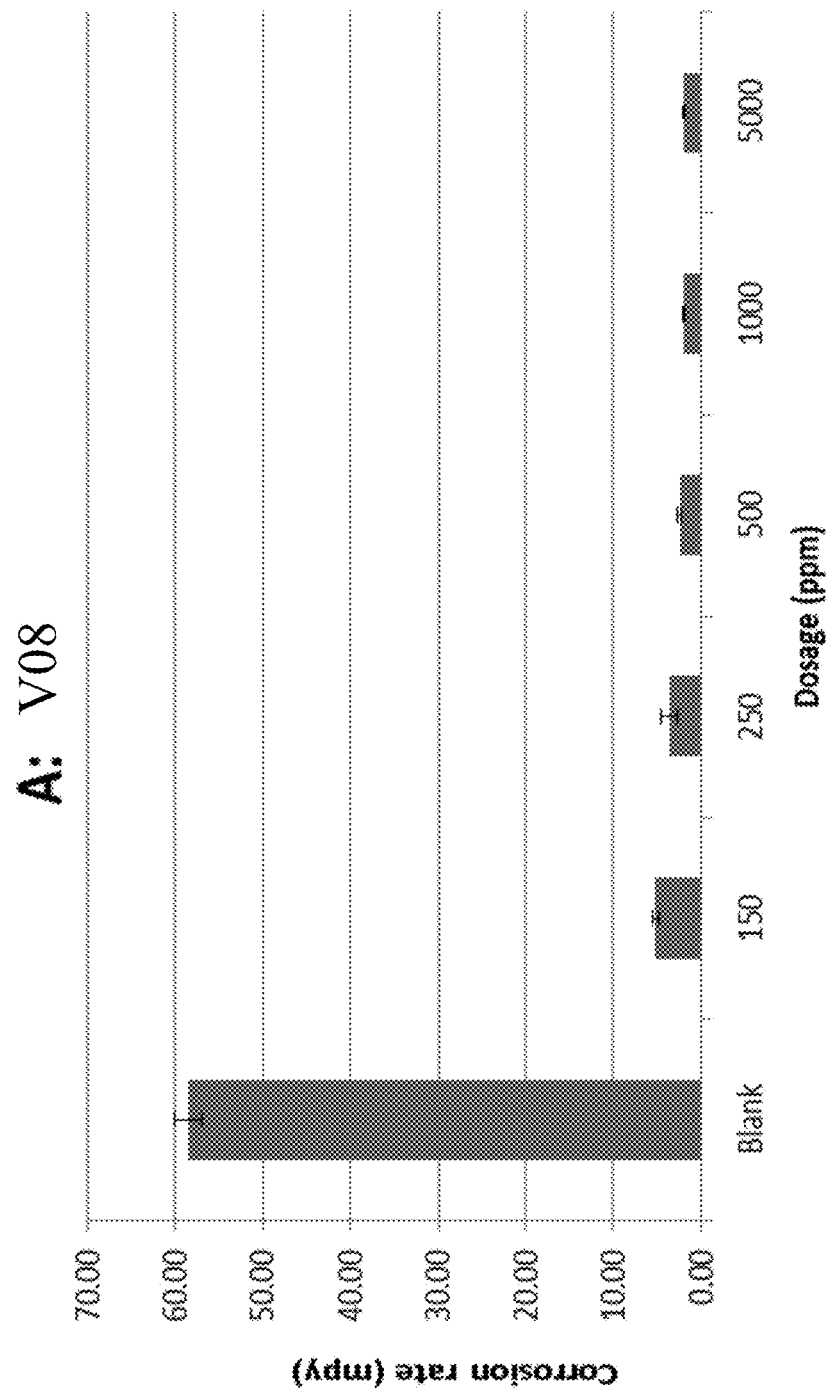
FIGS. 5A, 5B, and 5C depict graphs of corrosion rate versus concentration for V08, THPS, and glutaraldehyde.
Figure 5B:
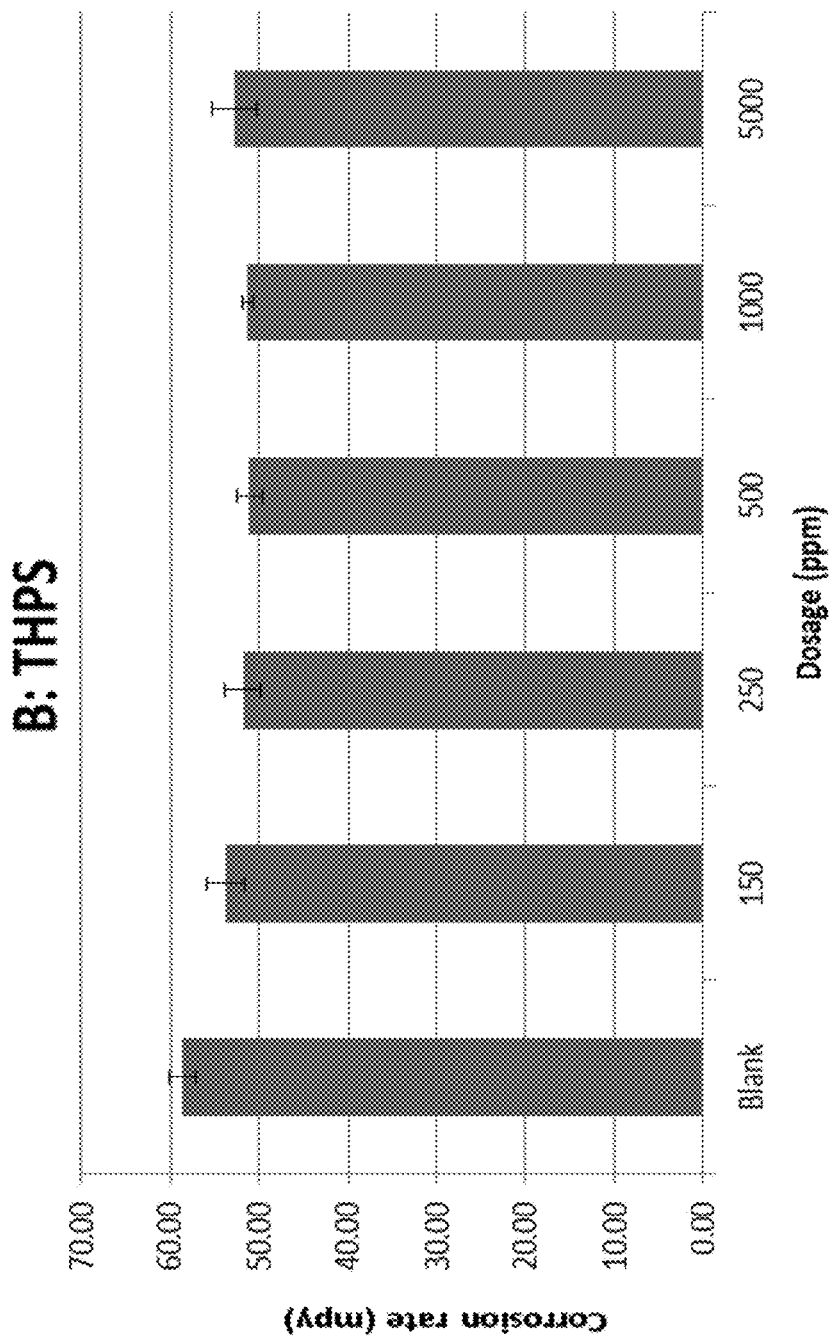
Figure 5C:
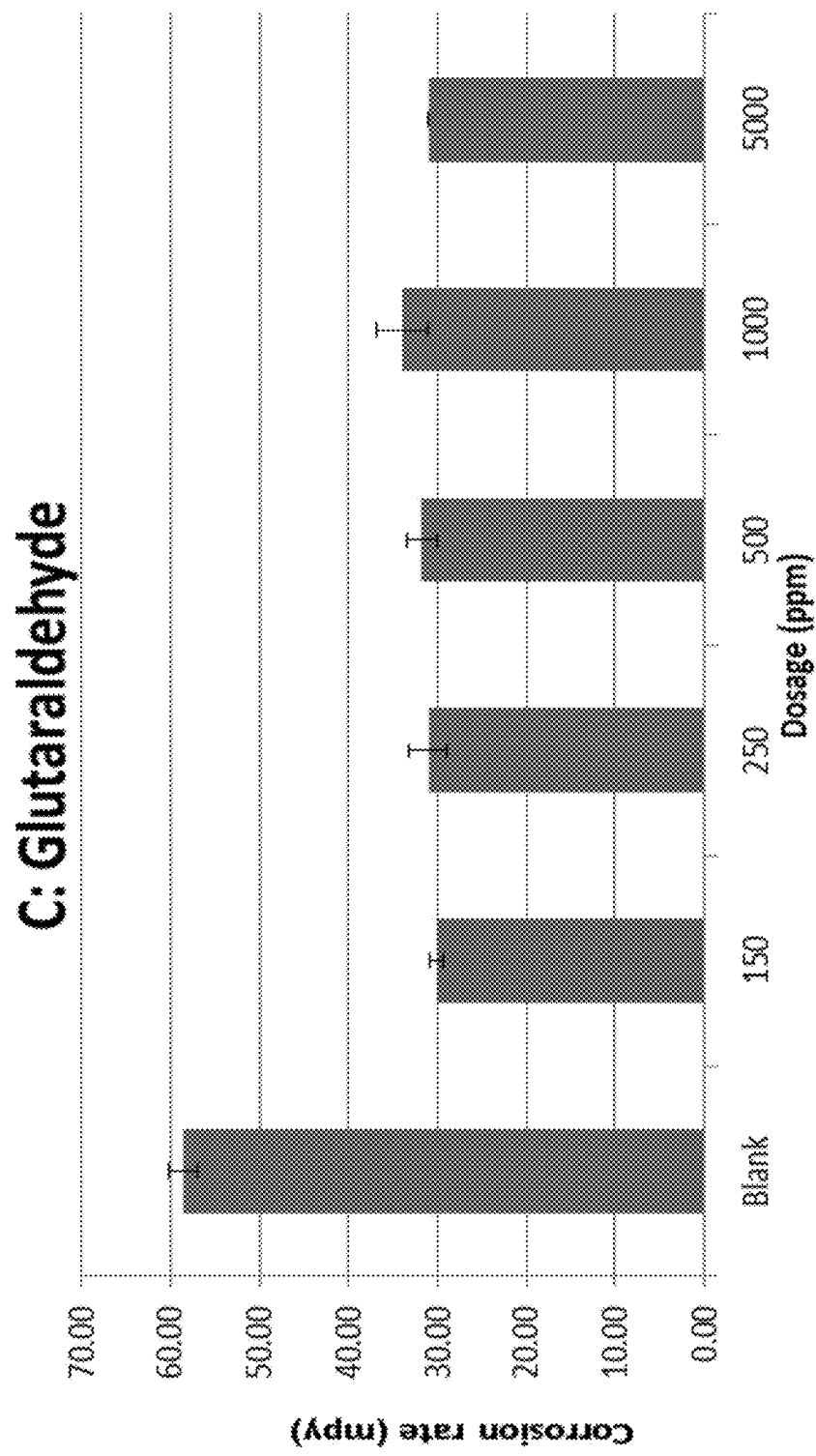

A study was conducted to assess the corrosiveness of the biocide and two other commonly used biocide products. In this evaluation the corrosion rates of C1018 carbon steel in $CO_2$ saturated brine at 100% water cut were monitored in the presence of various biocides at concentrations of up to 5,000 ppm using the wheel box corrosion test at 80° C. The results for the three biocide types, V08, 75% THPS, and 50% glutaraldehyde, are provided in FIG. 5 (A-C). All samples were run in triplicate. The blank or baseline corrosion rate in the 24 hour wheel box test provided an average corrosion rate of 58.60 mpy (mils penetration per year) while the 75% THPS and 50% glutaraldehyde biocides resulted in corrosion rates of 53.78 and 30.07 mpy, respectively. Similar trends emerged for THPS and glutaraldehyde as the concentration of each increased. However, V08 yielded a corrosion rate of 5.14 mpy at 100 ppm. The data indicated that the concentration of V08 is inversely proportional to the corrosion rate. The V08 product included water, 2-ethylhexanol, iso-propyl alcohol, Clean N Cor from Nalco, THPS, and acrylic acid, polymer with t-butylphenol, formaldehyde, maleic anhydride, propylene oxide, and ethylene oxide (CAS Registry Number: 178603-70-8). Overall the data revealed that V08 can provide corrosion protection.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:

1. A biocide composition an imidazoline compound; a quaternary amine; and a phosphonium compound; wherein the imidazoline compound has formula (I), (II), or (III),

(I)

(II)

(III)

wherein
$R^1$, $R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, —$COR^6$, —$CO_2R^7$, —$SO_3R^8$, —$PO_3H_2$, —$CON(R^9)(R^{10})$, —$OR^{11}$, and —$N(R^{12})(R^{13})$;

$R^2$ is a radical derived from a fatty acid;

$R^3$ and $R^x$ are independently selected from a radical derived from an unsaturated acid;

$R^6, R^7, R^8, R^9, R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, —$COR^{14}$, —$CO_2R^{15}$, -alkyl-$COR^{16}$, and -alkyl-$CO_2R^{17}$; and $R^{14}, R^{15}, R^{16}$, and $R^{17}$ are each independently, at each occurrence, selected from hydrogen, alkyl, and alkenyl.

2. The composition of claim 1, wherein the imidazoline compound has formula (I),

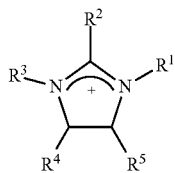

(I)

wherein $R^1, R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, —$COR^6$, —$CO_2R^7$, —$SO_3R^8$, —$PO_3H_2$, —$CON(R^9)(R^{10})$, —$OR^{11}$, and —$N(R^{12})(R^{13})$;

$R^2$ is a radical derived from a fatty acid;

$R^3$ is selected from a radical derived from an unsaturated acid;

$R^6, R^7, R^8, R^9, R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, —$COR^{14}$, —$CO_2R^{15}$, -alkyl-$COR^{16}$, and -alkyl-$CO_2R^{17}$; and $R^{14}, R^{15}, R^{16}$, and $R^{17}$ are each independently, at each occurrence, selected from hydrogen, alkyl, and alkenyl.

3. The composition of claim 2, wherein $R^1$ is unsubstituted $C_2$-$C_6$-alkyl;

$R^2$ is —$C_{17}H_{35}$, —$C_{17}H_{33}$, or —$C_{17}H_{31}$;

$R^3$ is —$CH_2CH_2CO_2R^e$, wherein $R^e$ is hydrogen, $C_1$-$C_6$-alkyl, or $R^e$ is absent;

$R^4$ is hydrogen; and $R^5$ is hydrogen.

4. The composition of claim 2, wherein $R^1$ is linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_{17}H_{33}$, or —$C_{17}H_{31}$;

$R^2$ is —$C_{17}H_{35}$, —$C_{17}H_{33}$, or —$C_{17}H_{31}$;

$R^3$ is —$CH_2CH_2CO_2R^e$, wherein $R^e$ is hydrogen, $C_1$-$C_6$-alkyl, or $R^e$ is absent;

$R^4$ is hydrogen; and $R^5$ is hydrogen.

5. The composition of claim 2, wherein $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or $R^{17}$ is absent;

$R^2$ is —$C_{17}H_{35}$, —$C_{17}H_{33}$, or —$C_{17}H_{31}$;

$R^3$ is —$CH_2CH_2CO_2R^e$, wherein $R^e$ is hydrogen, $C_1$-$C_6$-alkyl, or $R^e$ is absent;

$R^4$ is hydrogen; and $R^5$ is hydrogen.

6. The composition of claim 1, wherein the imidazoline compound has formula (II),

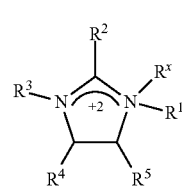

(II)

wherein $R^1, R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, —$COR^6$, —$CO_2R^7$, —$SO_3R^8$, —$PO_3H_2$, —$CON(R^9)(R^{10})$, —$OR^{11}$, and —$N(R^{12})(R^{13})$;

$R^2$ is a radical derived from a fatty acid;

$R^3$ and $R^x$ are each independently selected from a radical derived from an unsaturated acid;

$R^6, R^7, R^8, R^9, R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, —$COR^{14}$, —$CO_2R^{15}$, -alkyl-$COR^{16}$, and -alkyl-$CO_2R^{17}$; and $R^{14}, R^{15}, R^{16}$, and $R^{17}$ are each independently, at each occurrence, selected from hydrogen, alkyl, and alkenyl.

7. The composition of claim 6, wherein $R^1$ is unsubstituted $C_2$-$C_6$-alkyl;

$R^2$ is —$C_{17}H_{35}$, —$C_{17}H_{33}$, or —$C_{17}H_{31}$;

$R^3$ is —$CH_2CH_2CO_2R^e$, wherein $R^e$ is hydrogen, $C_1$-$C_6$-alkyl, or $R^e$ is absent;

$R^x$ is —$CH_2CH_2CO_2R^e$, wherein $R^e$ is hydrogen, $C_1$-$C_6$-alkyl, or $R^e$ is absent;

$R^4$ is hydrogen; and $R^5$ is hydrogen.

8. The composition of claim 6, wherein $R^1$ is linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_1H_{33}$, or —$C_{17}H_{31}$;

$R^2$ is —$C_{17}H_{35}$, —$C_{17}H_{33}$, or —$C_{17}H_{31}$;

$R^3$ is —$CH_2CH_2CO_2R^e$, wherein $R^e$ is hydrogen, $C_1$-$C_6$-alkyl, or $R^e$ is absent;

$R^x$ is —$CH_2CH_2CO_2R^e$, wherein $R^e$ is hydrogen, $C_1$-$C_6$-alkyl, or $R^e$ is absent;

$R^4$ is hydrogen; and $R^5$ is hydrogen.

9. The composition of claim 6, wherein $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or $R^{17}$ is absent;

$R^2$ is —$C_{17}H_{35}$, —$C_{17}H_{33}$, or —$C_{17}H_{31}$;

$R^3$ is —$CH_2CH_2CO_2R^e$, wherein $R^e$ is hydrogen, $C_1$-$C_6$-alkyl, or $R^e$ is absent;

$R^x$ is —$CH_2CH_2CO_2R^e$, wherein $R^e$ is hydrogen, $C_1$-$C_6$-alkyl, or $R^e$ is absent;

$R^4$ is hydrogen; and $R^5$ is hydrogen.

10. The composition of claim 1, wherein the imidazoline compound has formula (III),

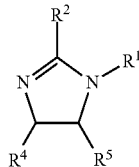

(III)

wherein $R^1$, $R^4$, and $R^5$ are each independently selected from hydrogen, alkyl, alkenyl, alkynyl, cycloalkyl, cycloalkenyl, aryl, heteroaryl, and heterocycle, said alkyl, alkenyl, alkynyl, cycloalkyl, cycloalkenyl, aryl, heteroaryl, and heterocycle each independently, at each occurrence, unsubstituted or substituted with 1 to 3 substituents independently selected from halogen, —$COR^6$, —$CO_2R^7$, —$SO_3R^8$, —$PO_3H_2$, —$CON(R^9)(R^{10})$, —$OR^{11}$, and —$N(R^{12})(R^{13})$;

$R^2$ is a radical derived from a fatty acid;

$R^6$, $R^7$, $R^8$, $R^9$, $R^{10}$, and $R^{11}$ are each independently, at each occurrence, selected from hydrogen, alkyl, and alkenyl;

$R^{12}$ and $R^{13}$ are each independently, at each occurrence, selected from hydrogen, alkyl, —$COR^{14}$, —$CO_2R^{15}$, -alkyl-$COR^{16}$, and -alkyl-$CO_2R^{17}$; and $R^{14}$, $R^{15}$, $R^{16}$, and $R^{17}$ are each independently, at each occurrence, selected from hydrogen, alkyl, and alkenyl.

11. The composition of claim 10, wherein $R^1$ is unsubstituted $C_2$-$C_6$-alkyl;

$R^2$ is —$C_{17}H_{35}$, —$C_{17}H_{33}$, or —$C_{17}H_{31}$;

$R^4$ is hydrogen; and $R^5$ is hydrogen.

12. The composition of claim 10, wherein $R^1$ is linear $C_2$-alkyl, substituted with one substituent that is a terminal —$N(R^{12})(R^{13})$, wherein $R^{12}$ is hydrogen and $R^{13}$ is —$COR^{14}$, wherein $R^{14}$ is —$C_{17}H_{35}$, —$C_1H_{33}$, or —$C_1H_{31}$;

$R^2$ is —$C_{17}H_{35}$, —$C_{17}H_{33}$, or —$C_{17}H_{31}$;

$R^4$ is hydrogen; and $R^5$ is hydrogen.

13. The composition of claim 10, wherein $R^1$ is linear $C_2$-alkyl, substituted with one substituent that is a terminal —$N(R^{12})(R^{13})$, wherein $R^{12}$ and $R^{13}$ are each a —$C_2$-alkyl-$CO_2R^{17}$, wherein $R^{17}$ is hydrogen or $R^{17}$ is absent;

$R^2$ is —$C_{17}H_{35}$, —$C_{17}H_{33}$, or —$C_{17}H_{31}$;

$R^4$ is hydrogen; and $R^5$ is hydrogen.

14. The composition of claim 1, wherein the quaternary amine has the formula

[$N^+R^{5a}R^{6a}R^{7a}R^{8a}$][$X^-$]

wherein $R^{5a}$, $R^{6a}$, $R^{7a}$, and $R^{8a}$ are each independently selected from substituted or unsubstituted $C_1$-$C_{18}$-alkyl; and X is Cl, Br or I.

15. The composition of claim 14, wherein $R^{5a}$, $R^{6a}$, $R^{7a}$, and $R^{8a}$ are each independently selected from the group consisting of unsubstituted $C_1$-$C_{18}$-alkyl, $C_1$-$C_{18}$-hydroxyalkyl, and benzyl.

16. The composition of claim 1, wherein the quaternary amine is selected from the group consisting of tetramethyl ammonium chloride, tetraethyl ammonium chloride, tetrapropyl ammonium chloride, tetrabutyl ammonium chloride, tetrahexyl ammonium chloride, tetraoctyl ammonium chloride, benzyltrimethyl ammonium chloride, benzyltriethyl ammonium chloride, phenyltrimethyl ammonium chloride, phenyltriethyl ammonium chloride, cetyl benzyldimethyl ammonium chloride, hexadecyl trimethyl ammonium chloride, dimethyl $C_{12-16}$-alkyl benzyl ammonium chloride, monomethyl di-$C_{12-16}$-alkyl benzyl quaternary ammonium chloride, benzyl triethanolamine quaternary ammonium chloride, benzyl dimethylaminoethanolamine quaternary ammonium chloride, cocoalkyl dimethyl benzyl ammonium chloride, and combinations thereof.

17. The composition of claim 1, wherein the phosphonium compound is selected from the group consisting of alkyltris(hydroxyorgano)phosphonium salts, alkenyltris(hydroxyorgano)phosphonium salts, tetrakis(hydroxyorgano)phosphonium salts, and combinations thereof.

18. The composition of claim 17, wherein the phosphonium compound is selected from the group consisting of $C_1$-$C_3$-alkyltris(hydroxymethyl)phosphonium salts, $C_2$-$C_3$-alkenyltris(hydroxymethyl)phosphonium salts, tetrakis(hydroxymethyl)phosphonium salts, and combinations thereof.

19. The composition of claim 18, wherein the phosphonium compound is selected from the group consisting of tetrakis(hydroxymethyl)phosphonium sulphate (THPS), tetrakis(hydroxymethyl)phosphonium chloride, tetrakis(hydroxymethyl)phosphonium phosphate, tetrakis(hydroxymethyl)phosphonium formate, tetrakis(hydroxymethyl)phosphonium acetate, tetrakis(hydroxymethyl)phosphonium oxalate, and combinations thereof.

20. The composition of claim 1, further comprising a demulsifier.

21. The composition of claim 20, wherein the demulsifier is selected from the group consisting of dodecylbenzylsulfonic acid (DDBSA), the sodium salt of xylenesulfonic acid (NAXSA), epoxylated and propoxylated compounds, anionic cationic and nonionic surfactants, and resins, phenolic and epoxide resins, and combinations thereof.

22. A method of controlling microbe proliferation in a system used in the production, transportation, storage, and separation of crude oil and natural gas, the method comprising contacting the system with an effective amount of a composition of claim 1.

* * * * *